(12) United States Patent
Ardehali et al.

(10) Patent No.: US 12,613,248 B2
(45) Date of Patent: Apr. 28, 2026

(54) FULL-LENGTH CILP AS A BIOMARKER FOR CARDIAC FIBROSIS

(71) Applicant: THE REGENTS OF THE UNIVERSITY OF CALIFORNIA, Oakland, CA (US)

(72) Inventors: Reza Ardehali, Los Angeles, CA (US); Shuin Park, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 776 days.

(21) Appl. No.: 17/995,266

(22) PCT Filed: Apr. 1, 2021

(86) PCT No.: PCT/US2021/070349
§ 371 (c)(1),
(2) Date: Sep. 30, 2022

(87) PCT Pub. No.: WO2021/203141
PCT Pub. Date: Oct. 7, 2021

(65) Prior Publication Data
US 2023/0152331 A1      May 18, 2023

Related U.S. Application Data

(60) Provisional application No. 63/004,351, filed on Apr. 2, 2020.

(51) Int. Cl.
*G01N 33/53*          (2006.01)
*C07K 14/78*          (2006.01)
*G01N 33/68*          (2006.01)

(52) U.S. Cl.
CPC ......... *G01N 33/6887* (2013.01); *C07K 14/78* (2013.01); *G01N 2800/325* (2013.01)

(58) Field of Classification Search
None
See application file for complete search history.

(56) References Cited

U.S. PATENT DOCUMENTS 7,211,649 B1      5/2007 Heinegard
2008/0241945 A1    10/2008 Lorenzo

OTHER PUBLICATIONS

Hinderer, Svenja, et al. Cardiac fibrosis—A short review of causes and therapeutic strategies, Advanced Drug Delivery Reviews, 146 (2019) 77-82. doi:10.1016/j.addr.2019.05.011.

Lehr, S, et al. Identification and validation of novel adipokines released from primary human adipocytes. Mol Cell Proteomics. Jan. 2012;11(1):M111.010504. doi: 10.1074/mcp.M111.010504. Epub Sep. 26, 2011. PMID: 21947364; PMCID: PMC3270100.

Shindo, Kazuhiro, et al. Cartilage Intermediate Layer Protein 1 Suppresses TGF-β Signaling in Cardiac Fibroblasts, International Journal of Gerontology, vol. 11, Issue 2, 2017, pp. 67-74, ISSN 1873-9598, https://doi.org/10.1016/j.ijge.2017.01.002. (https://www.sciencedirect.com/science/article/pii/S1873959817300066).

Van Nieuwenhoven, F.A., Munts, C., op't Veld, R.C et al. Cartilage intermediate layer protein 1 (CILP1): A novel mediator of cardiac extracellular matrix remodelling. Sci Rep 7, 16042 (2017). https://doi.org/10.1038/s41598-017-16201-y.

International Search Report for PCT/US21/70349 (WO2021203141 Published Oct. 7, 2021).

*Primary Examiner* — Gary Counts
(74) *Attorney, Agent, or Firm* — Karen S. Canady; canady + lortz LLP

(57) ABSTRACT

Methods for the detection, monitoring, and treatment of cardiac fibrosis, progression of cardiac fibrosis, or heart failure in a subject comprising: (a) contacting a sample obtained from the subject with a binding agent that binds a region of cartilage intermediate layer protein 1 (CILP) that spans the cleavage site of the CILP precursor or a nucleotide encoding same. The cardiac fibrosis may be associated with one or more of: ischemia, congenital defect, familial fibrosis, infiltrative fibrosis, idiopathic fibrosis, amyloidosis, hemosiderosis, valvular disease, and other idiopathic cardiomyopathies.

8 Claims, 10 Drawing Sheets

Specification includes a Sequence Listing.

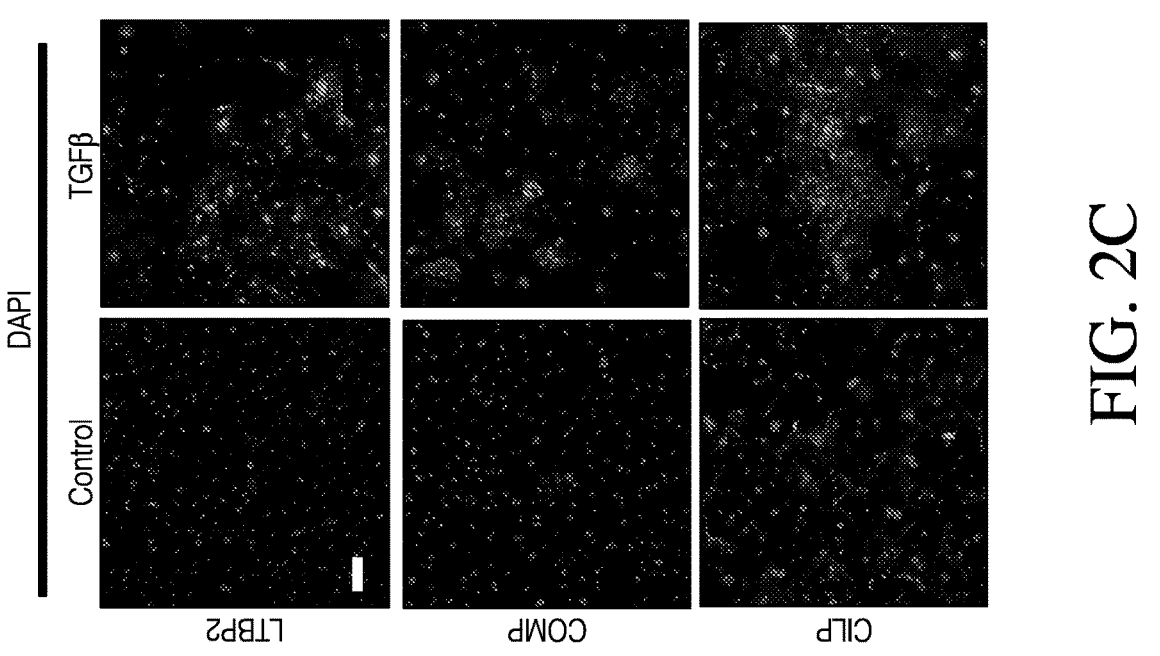
FIG. 2C
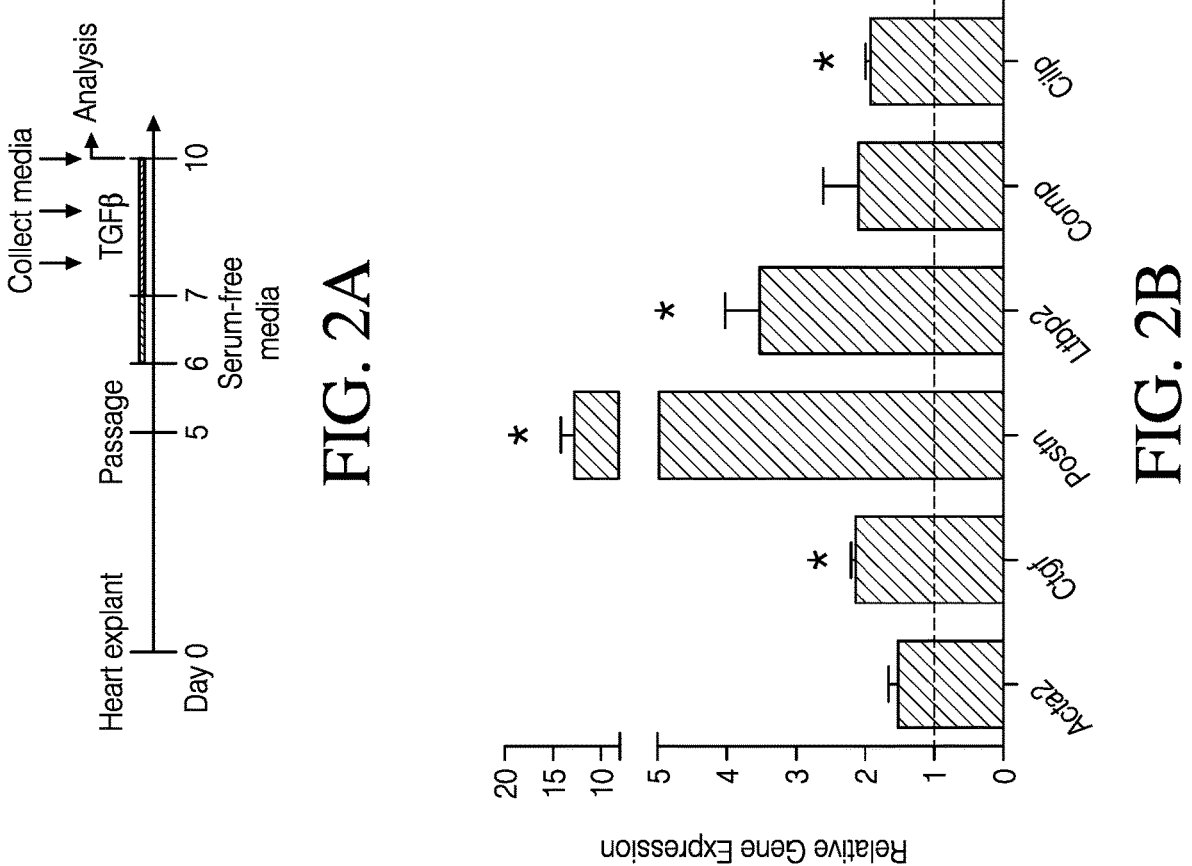
FIG. 2A
FIG. 2B

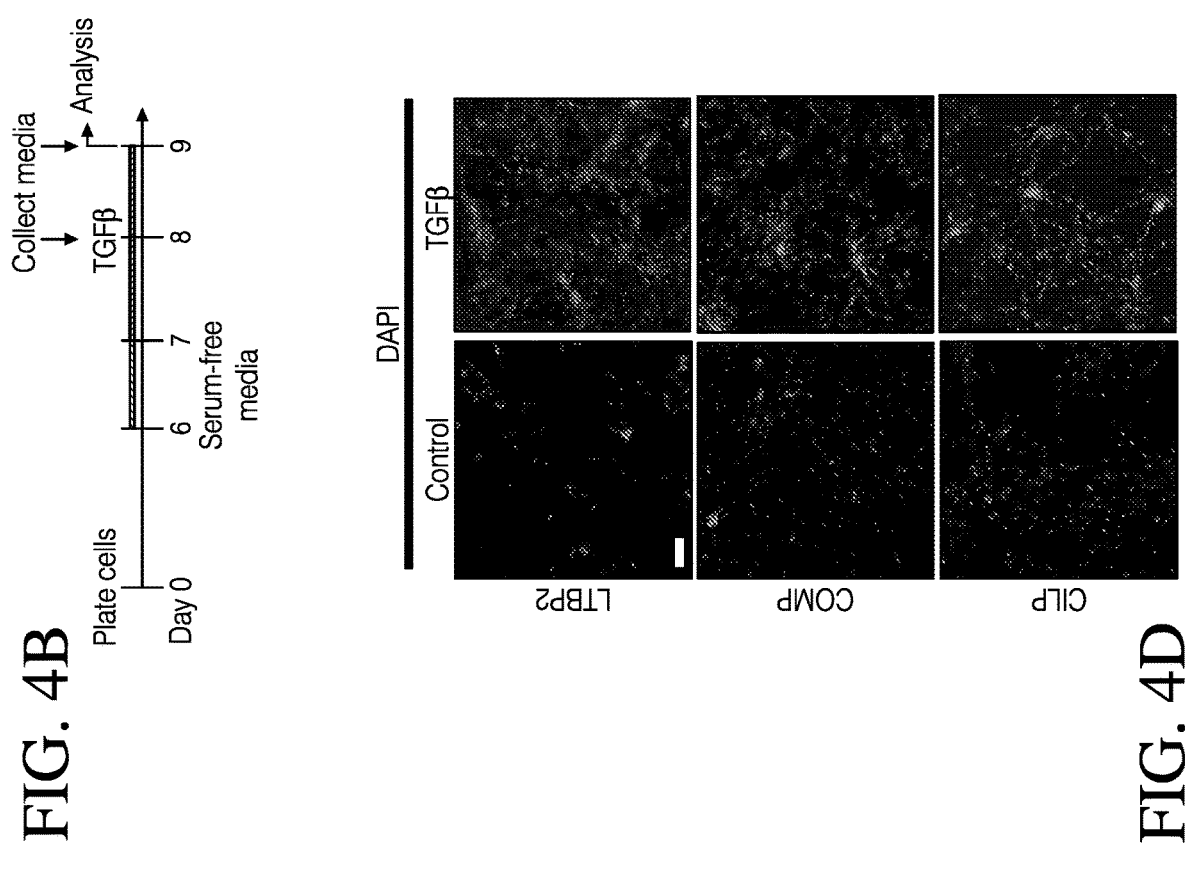
FIG. 4B
FIG. 4A
FIG. 4D
FIG. 4C
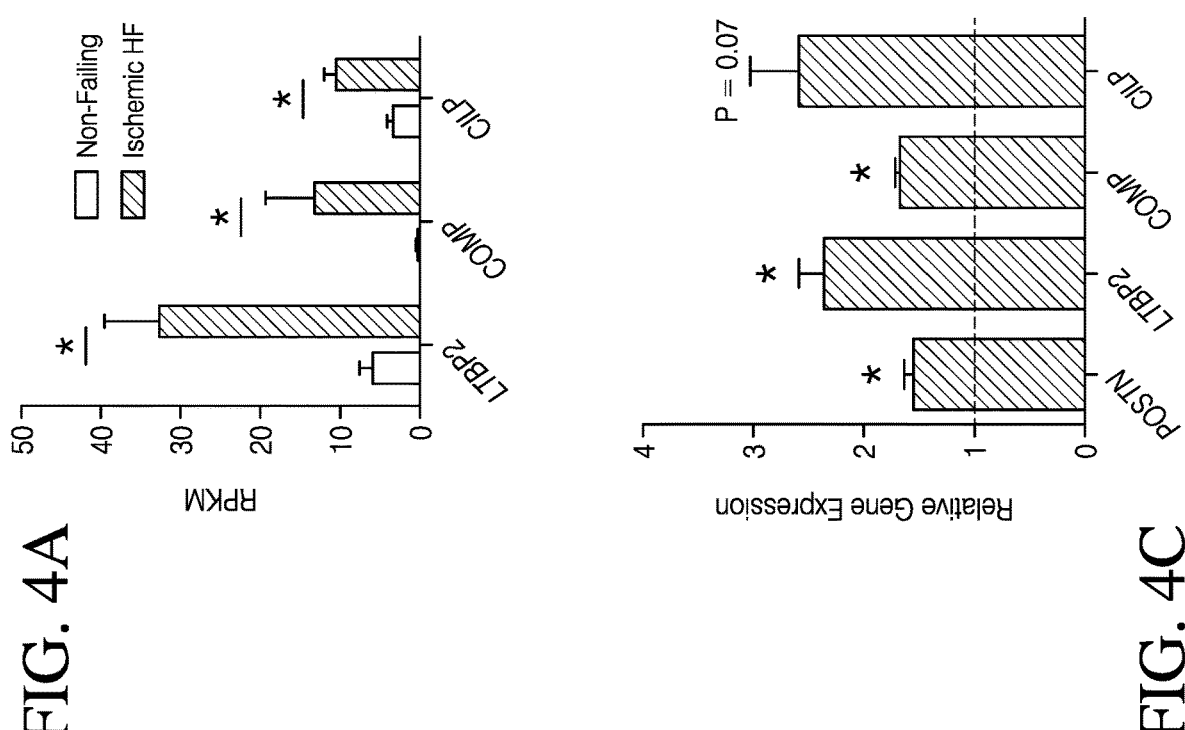

FULL-LENGTH CILP AS A BIOMARKER FOR CARDIAC FIBROSIS

This application claims benefit of U.S. provisional patent application No. 63/003,451, filed Apr. 1, 2020, the entire contents of which are incorporated by reference into this application.

ACKNOWLEDGEMENT OF GOVERNMENT SUPPORT

This invention was made with government support under Grant Number HL127728, awarded by the National Institutes of Health. The government has certain rights in the invention.

REFERENCE TO A SEQUENCE LISTING SUBMITTED VIA EFS-WEB

The content of the ASCII text file of the sequence listing named "UCLA280_seq" which is 15 kb in size was created on Mar. 25, 2021, and electronically submitted via EFS-Web herewith the application is incorporated herein by reference in its entirety.

BACKGROUND

Myocardial fibrosis is a pathological process associated with various forms of cardiac disease that contributes to impaired cardiac function, development of arrhythmias, and ultimately heart failure. Cardiac fibroblasts are the main participating cells in the development of myocardial fibrosis by their secretion of excess extracellular matrix proteins that contribute to scar tissue. There are currently limited treatment options for the reversal of cardiac fibrosis, and available therapies for heart failure are ineffective at preventing the formation of scar tissue.

There remains a need for identification of circulating biomarkers that can serve as a non-invasive clinical tool for determining the presence, extent, and progression of fibrosis in cardiac disease patients. In addition, there remains a need for such biomarkers that can aid in the prognosis and monitoring of cardiac fibrosis as an aid in the treatment and management of cardiac disease.

SUMMARY

The methods described herein provide for the detection, monitoring, and treatment of cardiac fibrosis, progression of cardiac fibrosis, or heart failure. The methods provide a non-invasive clinical tool for determining the presence, extent, and progression of fibrosis in a subject. In some embodiments, the method for detecting cardiac fibrosis, progression of cardiac fibrosis, or heart failure in a subject comprises: (a) contacting a sample obtained from the subject with a binding agent that binds a region of cartilage intermediate layer protein 1 (CILP) that spans the cleavage site of the CILP precursor or a nucleotide encoding same. In some embodiments, the nucleotide is a ribonucleic acid molecule (RNA). The method further comprises: (b) measuring the amount of CILP in the sample; and (c) detecting cardiac fibrosis, progression of cardiac fibrosis, or heart failure in the subject when the amount of CILP in the sample is decreased relative to a reference sample. In some embodiments, the method further comprises treating the subject for cardiac fibrosis, progression of cardiac fibrosis, or heart failure. In some embodiments, the sample is a serum sample.

In some embodiments, the method for treating cardiac fibrosis, progression of cardiac fibrosis, or heart failure in a subject comprises: (a) contacting a sample, such as, for example, a serum sample, obtained from the subject with a binding agent that binds a region of CILP that spans the cleavage site of the CILP precursor or a nucleotide encoding same; (b) measuring the amount of CILP in the sample; and (c) treating the subject for cardiac fibrosis, progression of cardiac fibrosis, or heart failure when the amount of CILP in the sample is decreased relative to a reference sample. In some embodiments, the cardiac fibrosis is associated with one or more of: ischemia, congenital defect, familial fibrosis, infiltrative fibrosis, idiopathic fibrosis, amyloidosis, hemosiderosis, valvular disease, and other idiopathic cardiomyopathies.

Also provided herein is a method for monitoring the status of cardiac fibrosis or heart failure in a subject. In some embodiments, the method comprises: (a) contacting a serum sample obtained from the subject with a binding agent that binds a region of CILP that spans the cleavage site of the CILP precursor or a nucleotide encoding same; (b) measuring the amount of CILP in the serum sample; and (c) adjusting treatment of the subject for cardiac fibrosis or heart failure when the amount of CILP in the serum sample is decreased relative to a reference sample, and making a corresponding adjustment to treatment of the subject for cardiac fibrosis or heart failure when the amount of CILP is equal to or increased relative to the reference sample. In some embodiments, adjusting treatment comprises changing classes of medication, switching medication, changing dosages (in some cases by increasing, and in some cases by decreasing). In some embodiments, adjusting treatment comprises administering, changing, or discontinuing a treatment as described herein. In some embodiments, the treatment comprises administering to the subject one or more of: angiotensin (AT)-converting enzymes, ATI receptor antagonists, β-blockers, Sacubitril/Valsartan, Aldosterone antagonists, statins, diuretics, or other medications/biologics (e.g., growth factor or cell therapy) effective for treating underlying heart failure and fibrosis.

In some embodiments, the reference sample is from a normal, healthy control subject. In some embodiments, the reference sample is a previously obtained sample from the subject.

In some embodiments, the binding agent is an antibody. In some embodiments, the antibody binds to full-length CILP. In some embodiments, the binding agent is a nucleic acid probe, such as for detection of RNA.

In some embodiments, the method further comprises measuring additional biomarkers. The additional biomarkers can include those described herein and/or other biomarkers of interest. In some embodiments, the additional biomarkers are a combination of one, two, three, four, or five biomarkers selected from B-type natriuretic peptide (BNP; or its stable precursor, NT-proBNP), Galectin-3 (Gal-3), suppression of tumorigenicity 2 (ST2), latent transforming growth factor beta (LTBP2), and cartilage oligomeric matrix protein (COMP). In some embodiments, up to 10 additional biomarkers are measured. In some embodiments, up to 3, 4, 5, 6, 7, 8, or 9 additional biomarkers are measured. In some embodiments, up to 15 or 20 additional biomarkers are measured. Also provided is a kit comprising reagents for use in detection of CILP, alone or together with additional biomarkers. In some embodiments, the kit comprises reagents for use in detecting up to 3, 5, 10, or 15 biomarkers, including CILP.

BRIEF DESCRIPTION OF THE DRAWINGS

FIGS. 2A-2C. LTBP2, COMP, and CILP are upregulated in cultured cardiac fibroblasts after TGFβ treatment. (2A) Schematic of cardiac fibroblast culture and TGFβ treatment. (2B) RT-qPCR of cardiac fibroblasts treated with TGFβ normalized to untreated controls (indicated by dotted line at y=1) (n=4). (2C) Immunocytochemistry for LTBP2, COMP, and CILP show significant increase in expression after TGFβ treatment (n=4). DAPI stained for nuclei. Scale bar: 100 μm. TGFβ: Transforming Growth Factor-β. P*<0.050 (t-test).

FIGS. 4A-4D. LTBP2, COMP, and CILP are upregulated in human cardiac fibroblasts in response to TGFβ. (4A) RNA-sequencing data from a public database (GSE46224) show that expression of LTBP2, COMP, and CILP are upregulated in heart biopsies from ischemic heart failure (HF) patients compared to healthy patients. (4B) Schematic of culture and TGFβ treatment of human cardiac fibroblasts. (4C) RT-qPCR of human cardiac fibroblasts treated with TGFβ normalized to untreated controls (indicated by dotted line at y=1) (n=3). (4D) Immunocytochemistry shows increased expression of LTBP2, COMP, and CILP in cultured human cardiac fibroblasts after TGFβ treatment. DAPI stained for nuclei (n=4). RPKM: Reads Per Kilobases Mapped. Scale bar: 100 μm. *P<0.050 (t-test).

(7A) Schematic of cardiac fibroblast sort, culture and TGFβ treatment. (7B) Immunocytochemistry show that TGFβ treatment induces increased expression of LTBP2, COMP, and CILP. DAPI stained for nuclei. Scale bar: 100 μm. TGFβ: Transforming Growth Factor-β

Figure 8:
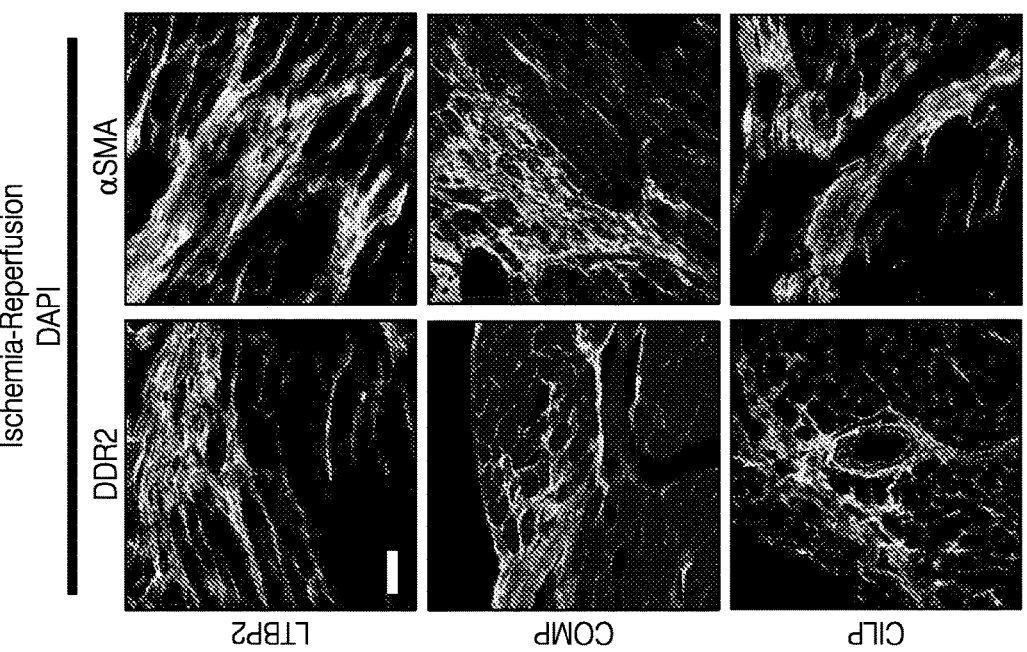

FIG. 8. Expression of LTBP2, COMP, and CILP are elevated in ischemia-reperfusion injury. Immunofluorescence staining of heart sections from mice that had undergone ischemia-reperfusion injury shows colocalization of LTBP2, COMP, and CILP with fibroblast marker DDR2 and activated fibroblast marker αSMA. DAPI stained for nuclei. Scale bar: 50 μm. DDR2: Discoidin Domain Receptor Tyrosine Kinase 2. αSMA: α-Smooth Muscle Actin.

Figures 9A, 9B, 9C:
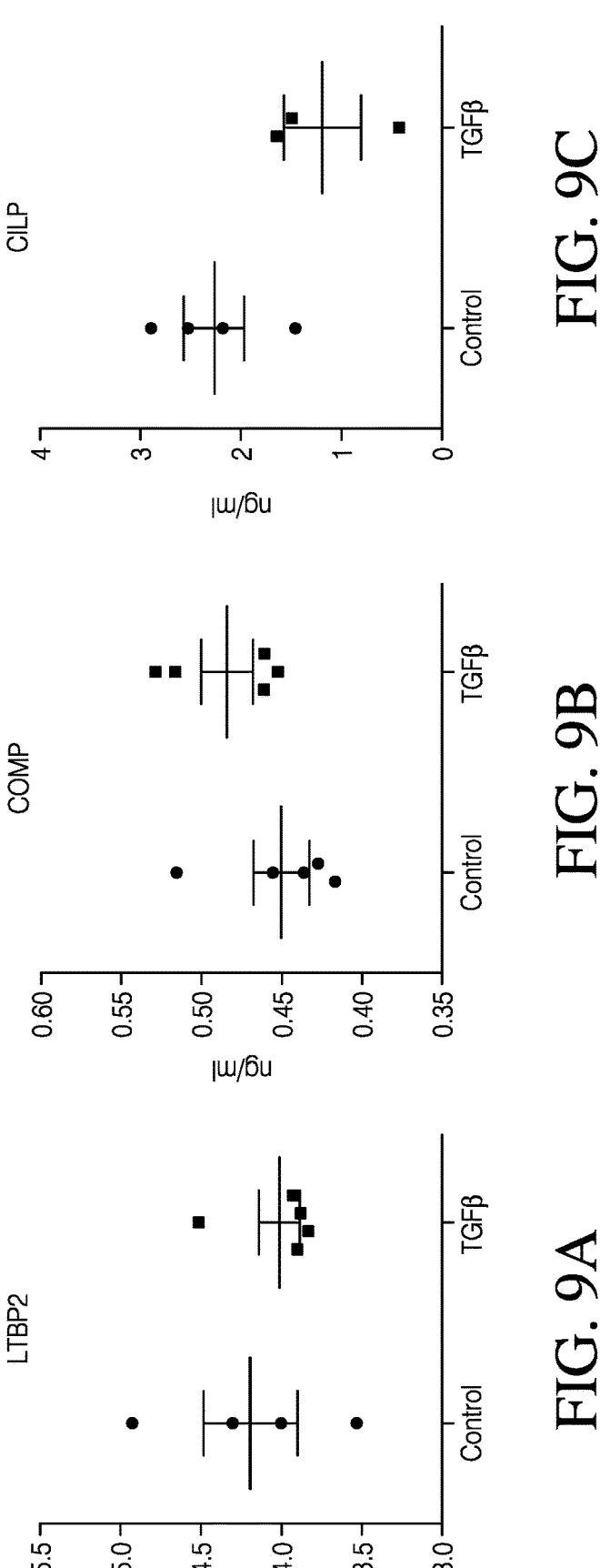

FIGS. 9A-9C. Levels of LTBP2, COMP, and CILP in conditioned media from cultured human CFbs. There were no statistically significant differences in levels of LTBP2 (9A), COMP (9B), and CILP (9C) in collected media from human CFbs treated with TGFβ (n=3-5).

Figure 10:
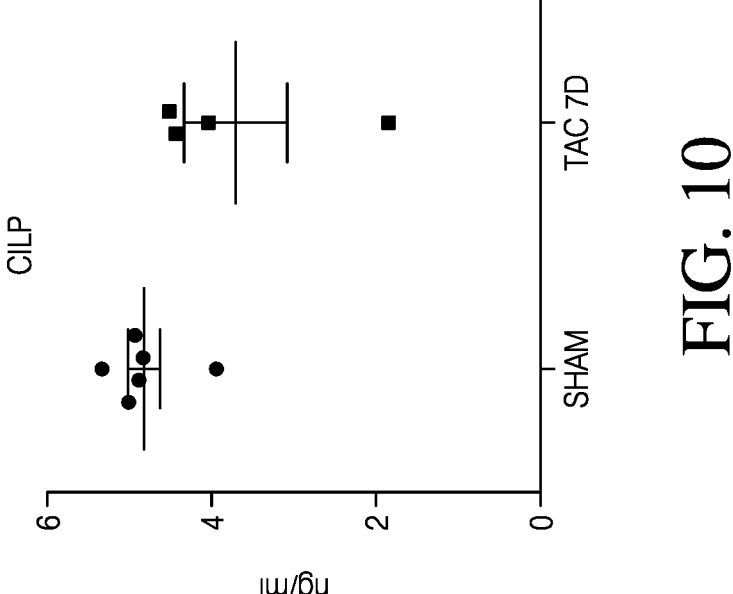

FIG. 10. CILP levels are decreased in the serum of mice that have undergone TAC. ELISA demonstrate a decrease in levels of CILP in the serum of mice 7 days after TAC surgery (n=4-6).

DETAILED DESCRIPTION

The invention described herein is based on the surprising discovery that the full length CILP protein provides a circulating biomarker for cardiac fibrosis. Serum from heart failure patients exhibited significantly decreased levels of CILP compared to serum from healthy volunteers when measured by ELISA. The CILP gene encodes a precursor protein that undergoes cleavage into an N-terminal fragment of roughly 75 kDa and a C-terminal fragment of about 55 kDa (7). Both fragments were shown to inhibit Smad3 phosphorylation, which is normally promoted by active TGFβ signaling. While commercially available ELISA kits target the C-terminal region of CILP (hence detecting both the C-terminal and the full-length fragment), previous work showed that cardiac fibroblasts secrete the N-terminal fragment as well as the full-length CILP protein. As described herein, use of an antibody that spans the cleavage site of the CILP precursor and western blotting levels of circulating full-length CILP, the studies described herein showed that serum from heart failure patients had significantly decreased levels of full-length CILP in circulation.

The invention provides new methods for detection, monitoring, and treatment of cardiac fibrosis, progression of cardiac fibrosis, and heart failure.

Definitions

All scientific and technical terms used in this application have meanings commonly used in the art unless otherwise specified. As used in this application, the following words or phrases have the meanings specified.

As used herein, a "control" or "reference" sample means a sample that is representative of normal measures of the respective marker, such as would be obtained from normal, healthy control subjects, or a baseline amount of marker to be used for comparison. Typically, a baseline will be a measurement taken from the same subject or patient. The sample can be an actual sample used for testing, or a reference level or range, based on known normal measurements of the corresponding marker.

As used herein, a "significant difference" means a difference that can be detected in a manner that is considered reliable by one skilled in the art, such as a statistically significant difference, or a difference that is of sufficient magnitude that, under the circumstances, can be detected with a reasonable level of reliability. In one example, an increase or decrease of 10% relative to a reference sample is a significant difference. In other examples, an increase or decrease of 20%, 30%, 40%, or 50% relative to the reference sample is considered a significant difference. In yet another example, an increase of two-fold relative to a reference sample is considered significant.

"Nucleotide sequence" refers to a heteropolymer of deoxyribonucleotides, ribonucleotides, or peptide-nucleic acid sequences that may be assembled from smaller fragments, isolated from larger fragments, or chemically synthesized de novo or partially synthesized by combining shorter oligonucleotide linkers, or from a series of oligonucleotides, to provide a sequence which is capable of expressing the encoded protein.

The term "primer," as used herein, means an oligonucleotide designed to flank a region of DNA to be amplified. In a primer pair, one primer is complementary to nucleotides present on the sense strand at one end of a polynucleotide fragment to be amplified and another primer is complementary to nucleotides present on the antisense strand at the other end of the polynucleotide fragment to be amplified. A primer can have at least about 11 nucleotides, and preferably, at least about 16 nucleotides and no more than about 35 nucleotides. Typically, a primer has at least about 80% sequence identity, preferably at least about 90% sequence identity with a target polynucleotide to which the primer hybridizes.

As used herein, the term "probe" refers to an oligonucleotide, naturally or synthetically produced, via recombinant methods or by PCR amplification, that hybridizes to at least part of another oligonucleotide of interest. A probe can be single-stranded or double-stranded.

As used herein, the term "active fragment" refers to a substantial portion of an oligonucleotide that is capable of performing the same function of specifically hybridizing to a target polynucleotide.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to those skilled in the art. The nucleotide sequence of a target polynucleotide is generally a sequence complementary to the oligonucleotide primer or probe. The hybridizing oligonucleotide may contain nonhybridizing nucleotides that do not interfere with forming the noncovalent interaction. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target sequence as long as there is hybridization under standard hybridization conditions.

The term "complement" and "complementary" as used herein, refers to the ability of two DNA molecules to base pair with each other, where an adenine on one DNA molecule will base pair to a guanine on a second DNA molecule and a cytosine on one DNA molecule will base pair to a thymine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5'-GCAT are complementary, and the complement of the DNA molecule 5'-ATGC is 5'-GCAT. The term complement and complementary also encompasses two DNA molecules where one DNA molecule contains at least one nucleotide that will not base pair to at least one nucleotide present on a second DNA molecule. For instance, the third nucleotide of each of the two DNA molecules 5'-ATTGC and 5'-GCTAT will not base pair, but these two DNA molecules are complementary as defined herein. Typically, two DNA molecules are complementary if they hybridize under the standard conditions referred to above. Typically, two DNA molecules are complementary if they have at least about 80% sequence identity, preferably at least about 90% sequence identity.

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, *Remington's Pharmaceutical Sciences,* 18th edition, A. Gennaro, ed., Mack Publishing Co., Easton, PA, 1990).

As used herein, the term "subject" includes any human or non-human animal. The term "non-human animal" includes all vertebrates, e.g., mammals and non-mammals, such as non-human primates, horses, sheep, dogs, cows, pigs, chickens, and other veterinary subjects. In a typical embodiment, the subject is a human.

As used herein, "a" or "an" means at least one, unless clearly indicated otherwise.

Methods

The invention provides methods for the detection, monitoring, and treatment of cardiac fibrosis, optionally including progression of cardiac fibrosis, or heart failure. In some embodiments, the method for detecting cardiac fibrosis, progression of cardiac fibrosis, or heart failure in a subject comprises: (a) contacting a sample obtained from the subject with a binding agent that binds a region of cartilage intermediate layer protein 1 (CILP; UniProt O75339; SEQ ID NO: 1) that spans the cleavage site of the CILP precursor or a nucleotide encoding same. In some embodiments, the binding agent detects the presence of full-length CILP. The binding agent, by binding a region of CILP that spans the cleavage site, is capable of distinguishing between the detection of full-length CILP and its 55 kDa C-terminal fragment. The two peptides that CILP is cleaved into are known as CILP protein 1 C1 and C2, and the cleavage site is at amino acid 724 of SEQ ID NO: 1. In one embodiment, the binding agent targets Pro604 to His864 of SEQ ID NO: 1.

In some embodiments, the nucleotide is a ribonucleic acid molecule (RNA). The method further comprises: (b) measuring the amount of CILP in the sample; and (c) detecting cardiac fibrosis, progression of cardiac fibrosis, or heart failure in the subject when the amount of CILP (or RNA encoding same) in the sample is decreased relative to a reference sample. In some embodiments, the method further comprises treating the subject for cardiac fibrosis, progression of cardiac fibrosis, or heart failure. In some embodiments, the method for detecting cardiac fibrosis or heart failure in a subject comprises: (a) contacting a sample obtained from the subject with a binding agent that binds a region of CILP precursor. In some embodiments, the binding agent detects the presence of full-length CILP. The method further comprises: (b) measuring the amount of CILP in the sample; and (c) detecting cardiac fibrosis, progression of cardiac fibrosis, or heart failure in the subject when the amount of CILP in the sample is decreased relative to a reference sample.

In some embodiments, the method for treating cardiac fibrosis, progression of cardiac fibrosis, or heart failure in a subject comprises: (a) contacting a sample obtained from the subject with a binding agent that binds a region of CILP that spans the cleavage site of the CILP precursor or a nucleotide encoding same; (b) measuring the amount of CILP in the sample; and (c) treating the subject for cardiac fibrosis, progression of cardiac fibrosis, or heart failure when the amount of CILP in the sample is decreased relative to a reference sample. In some embodiments, the treatment comprises administering to the subject one or more of: angiotensin (AT)-converting enzymes, ATI receptor antagonists, β-blockers, Sacubitril/Valsartan, Aldosterone antagonists, statins, diuretics, or other medications/biologics (e.g., growth factor or cell therapy) effective for treating underlying heart failure and fibrosis. In some embodiments, the cardiac fibrosis is associated with one or more of: ischemia, congenital defect, familial fibrosis, infiltrative fibrosis, idiopathic fibrosis, amyloidosis, hemosiderosis, valvular disease, and other idiopathic cardiomyopathies.

Also provided herein is a method for monitoring the status of cardiac fibrosis or heart failure in a subject. In some embodiments, the method comprises: (a) contacting a sample obtained from the subject with a binding agent that binds a region of CILP that spans the cleavage site of the CILP precursor or a nucleotide encoding same; (b) measuring the amount of CILP in the sample; and (c) adjusting treatment of the subject for cardiac fibrosis or heart failure when the amount of CILP in the sample is decreased relative to a reference sample, and making a corresponding adjustment to treatment of the subject for cardiac fibrosis or heart failure when the amount of CILP is equal to or increased relative to the reference sample. In some embodiments, adjusting treatment comprises administering, changing, or discontinuing a treatment as described herein. In some embodiments, adjusting treatment comprises changing classes of medication, switching medication, changing dosages (in some cases by increasing, and in some cases by decreasing). Representative examples of adjusting treatment include, but are not limited to, starting or increasing angiotensin (AT)-converting enzymes, ATI receptor antagonists, β-blockers, Sacubitril/Valsartan, Aldosterone antagonists, statins, diuretics, or other medications/biologics (e.g., growth factor or cell therapy).

In some embodiments, the reference sample is from a normal, healthy control subject. In some embodiments, the reference sample is from the same subject, such as a previously obtained sample from the subject. Such samesubject samples can be useful, for example, in monitoring a subject's progress and ensuring recovery.

For use in the methods described herein, representative examples of the sample include, but are not limited to, blood, plasma or serum, tissue, cell cultures, and other bodily fluids or tissue specimens. In a typical embodiment, the sample is serum.

In some embodiments, the binding agent is an antibody. In some embodiments, the antibody binds to full-length CILP. In some embodiments, the binding agent is a nucleic acid probe, such as for detection of RNA.

In some embodiments, the method further comprises measuring additional biomarkers. In some embodiments, the additional biomarkers are serum biomarkers. In some embodiments, the additional biomarkers are suitable for use with tissue samples or biopsy material. In some embodiments, the additional biomarkers include one or more of: B-type natriuretic peptide (BNP; or its stable precursor, NT-proBNP), Galectin-3 (Gal-3), suppression of tumorigenicity 2 (ST2), latent transforming growth factor beta (LTBP2), and cartilage oligomeric matrix protein (COMP). In some embodiments, up to 10 additional biomarkers are measured. In some embodiments, up to 3, 4, 5, 6, 7, 8, or 9 additional biomarkers are measured. In some embodiments, up to 15 or 20 additional biomarkers are measured.

Kits and Assay Standards

The invention provides a kit comprising reagents for use in detection of CILP, alone or together with additional biomarkers. In some embodiments, the kit comprises reagents for use in detecting up to 2, 3, 4, 5, 6, 7, 8, 9, 10, 12, 15, 20, or up to 25 biomarkers, including CILP. In some embodiments, the additional biomarkers include one or more of: B-type natriuretic peptide (BNP; or its stable precursor, NT-proBNP), Galectin-3 (Gal-3), suppression of tumorigenicity 2 (ST2), latent transforming growth factor beta (LTBP2), and cartilage oligomeric matrix protein (COMP).

Provided are kits comprising a set of reagents as described herein, such as antibodies that specifically bind one or more markers of the invention (including genes and their expression products), and optionally, one or more suitable containers containing reagents of the invention. Reagents include molecules that specifically bind and/or amplify and/or detect one or more markers of the invention. Such molecules can be provided in the form of a microarray or other article of manufacture for use in an assay described herein. One example of a reagent is an antibody or nucleic acid probe that is specific for the marker(s). Another example includes probes (or primers) that selectively identify one or more genotypes described herein. Reagents can optionally include a detectable label. Labels can be fluorescent, luminescent, enzymatic, chromogenic, or radioactive.

Kits of the invention optionally comprise an assay standard or a set of assay standards, either separately or together with other reagents. An assay standard can serve as a normal control by providing a reference level of normal expression for a given marker that is representative of a healthy individual.

Kits can include probes for detection of alternative gene expression products in addition to antibodies for protein detection. The kit can optionally include a buffer. Reagents and standards can be provided in combinations reflecting the combinations of markers described herein as useful for detection.

EXAMPLES

The following examples are presented to illustrate the present invention and to assist one of ordinary skill in making and using the same. The examples are not intended in any way to otherwise limit the scope of the invention.

Example 1: Cardiac Fibrosis is Associated with Decreased Circulating Levels of Full-Length CILP in Heart Failure This Example identifies circulating biomarkers for cardiac fibrosis. This Example demonstrates that, upon in vitro stimulation or in vivo pressure overload injury, activated cardiac fibroblasts express LTBP2, COMP, and CILP. Further, in ischemic heart disease, LTBP2, COMP, and CILP localize to the fibrotic regions of the injured heart. The results show that circulating levels of full-length CILP protein are decreased in heart failure patients, supporting the use of this protein as a biomarker for the presence of cardiac fibrosis.

Cardiac fibrosis leads to pathological remodeling that can deteriorate cardiac function. Heart failure arising from cardiac fibrosis is a debilitating syndrome, and there is a need to identify circulating biomarkers that can help diagnose the extent of fibrosis.

We performed experimental pressure overload injury in C57BL/6J mice by transverse aortic constriction (TAC) and isolated cardiac fibroblasts 7 days post injury or sham operation for RNA-sequencing. Potential biomarkers for cardiac fibrosis were identified and results confirmed by reverse transcription-qPCR. Expression of the biomarkers were measured in fibroblasts treated in vitro with TGFβ by immunocytochemistry. Immunofluorescence staining confirmed expression in hearts from TAC murine hearts and human heart failure biopsies. Circulating protein levels were measured by ELISA and Western blotting of serum from human subjects.

The results showed that LTBP2, COMP, and CILP were upregulated in murine and human cardiac fibroblasts after in vitro TGFβ treatment. All three proteins were found to be expressed specifically in the fibrotic regions of injured murine and human hearts. Additionally, the full-length CILP protein showed a significant decrease in circulating levels in heart failure patients compared to healthy volunteers.

The full-length CILP protein thus provides a circulating biomarker for cardiac fibrosis. LTBP2 and COMP are additional markers that specifically localized to the fibrotic regions of the injured myocardium. Further studies are warranted to determine the functional contributions of these proteins to the development of cardiac fibrosis.

Abbreviations Used:

CFb: Cardiac Fibroblasts

ECM: Extracellular Matrix

TAC: Transverse Aortic Constriction

RNA: Ribonucleic Acid

LTBP2: Latent TGFβ-binding Protein

TGFβ: Transforming Growth Factor-Beta

COMP: Cartilage Oligomeric Matrix Protein

CILP: Cartilage Intermediate Layer Protein

RT-qPCR: Reverse Transcription-quantitative PCR

IF: Immunofluorescence

ICC: Immunocytochemistry

ELISA: Enzyme-linked immunosorbent assay

Myocardial fibrosis is a pathological process associated with various forms of cardiac disease that contributes to impaired cardiac function, development of arrhythmias, and ultimately heart failure (1,2). The formation of fibrosis can be initiated by either an acute ischemic event to the heart, such as myocardial infarction, or through a chronic progression driven by increased cardiac load. Cardiac fibroblasts (CFbs) are the main participating cells in the development of myocardial fibrosis (3). Under homeostatic conditions, resident CFbs are responsible for maintaining the structural integrity of the heart by regulating extracellular matrix (ECM) production (4). However, under pathological conditions, CFbs become activated, proliferate, and secrete an excess amount of ECM proteins, contributing to scar tissue (3,4). This scar replaces healthy myocardium, renders the substrate arrhythmogenic, induces stiffening of the heart and leads to adverse remodeling. Collectively, the sequela of fibrosis can have deleterious effects on the ability of the heart to pump blood effectively and hinders the recovery of cardiac function. There are currently limited treatment options for the reversal of cardiac fibrosis, and available therapies for heart failure are ineffective at preventing the formation of scar tissue (5). It has been suggested that identifying diagnostic markers for fibrosis may provide prognostic value for clinicians (6). Considering the critical role of CFbs in myocardial fibrosis, we hypothesized that CFbs may release factors that could serve as promising biomarkers for cardiac fibrosis (7). Identification of circulating biomarkers would serve as a non-invasive clinical tool of determining the presence, extent, and progression of fibrosis in cardiac disease patients.

In the present Example, we isolated CFbs from C57BL/6J mice that underwent transverse aortic constriction (TAC, a pressure overload injury model) or sham operation and performed RNA-sequencing to identify key upregulated genes in response to injury (8). From this data, we identified three genes encoding secreted proteins that could be potential biomarkers for myocardial fibrosis: latent TGFβ-binding protein 2 (Ltbp2), cartilage oligomeric matrix protein (Comp), and cartilage intermediate layer protein 1 (Cilp). Ltbp2 is part of the latent TGFβ-binding protein family, which consists of key regulators of TGFβ signaling (9). Comp and Cilp are mainly known for their roles in the binding of specific ECM proteins, such as collagens, in cartilage (10,11). LTBP2, COMP, and CILP were upregulated in cultured murine CFbs and in the fibrotic regions of TAC hearts, suggesting that their expression is specific to the formation of scar. Furthermore, there was an increase in expression of these proteins in stimulated human CFbs and within the fibrotic regions of heart sections from heart failure patients, demonstrating their potential as clinical biomarkers for fibrosis. Finally, we show that CILP, specifically the full length CILP protein, demonstrated a significant difference in circulating levels in the serum of mice after TAC and heart failure patients. The findings in this study introduce potential markers for myocardial fibrosis and support the need to pursue studies on CILP as a possible circulating biomarker for the development of cardiac fibrosis.

Methods

Study Approvals

All mouse surgery procedures were carried out with the approval of the University of California, Los Angeles (UCLA) Animal Research Committee or the Institutional Animal Care. The study was approved by an IRB (12-001164) and human participants gave written informed consent.

RNA-Sequencing and Analysis

Cardiac fibroblasts were isolated from murine hearts, as previously described, for RNA-sequencing (8). This data is publicly available on GEO (GSE51620). Downstream analysis was conducted using the DESeq2, Enhanced Volcanoplot and gplots R packages (12,13). Detailed strategy for identifying potential gene targets is described in the Supplementary Methods presented in Example 2 below.

Mice

Adult C57BL/6J mice (age 8-12 weeks) were used for all experiments. For the in vivo experiments, mice were randomly assigned into sham, TAC, and ischemic reperfusion (IR) treatment groups. No phenotypic differences were observed between male and female mice. Details of surgery are described in the Example 2. All procedures were carried out with the approval of the University of California, Los Angeles (UCLA) Animal Research Committee or the Institutional Animal Care.

Cardiac Fibroblast Culture and TGFβ Treatment (Murine and Human)

For mouse explant fibroblast cultures, hearts were collected, digested, and plated as described in Example 2 below. Twelve hours after plating, the floating cells were removed, and the media was replaced. Media changes were done every other day until cells reached 80% confluency, at which point they were passaged and cultured in serum-free media for 24 hours prior to TGFβ treatment (Cell Signaling, 50 ng/mL). Throughout the TGFβ treatment, the media was changed daily. Human fibroblasts were cultured according to the company's instructions (Cell Applications) and similarly passaged for TGFβ treatment (R&D Systems, 10 ng/mL).

RNA Extraction and RT-qPCR

RNA was extracted from cells using TRIzol™ LS Reagent (ThermoFisher) and following the manufacturer's instructions. RNA was quantified by NanoDrop, and cDNA was prepared using the iScript™ Reverse Transcription Supermix kit (Bio-Rad). Reverse transcription quantitative-PCR (RT-qPCR) reactions were prepared using SYBR Green (Bio-Rad) and primers (IDT) unique for each gene of interest (Table 1). The reactions were run on a CFX96™ Real-Time PCR Detection System and relative gene expression data was calculated by double delta CT analysis.

Immunocytochemical/Immunofluorescence Staining

Cells were cultured on 8-well chamber slides (Falcon) and washed with PBS prior to fixation with 4% paraformaldehyde (PFA). For in vivo staining, murine hearts were isolated and fixed with 4% PFA overnight prior to being incubated in 30% sucrose and embedded in Optimal Cutting Temperature (OCT) compound (Fisher). Hearts were sectioned at a thickness of 8 μm in a cryostat, mounted on Colorfrost Plus microscope slides (Fisher), and stored at −20° C. until ready to stain. Detailed staining protocol is provided in Example 2 below. Slides were incubated with antibodies outlined in Table 2.

ELISA and Western Blot

Protocols for conditioned media and serum sample preparation are described in Example 2 below. ELISA kits were purchased from MyBiosource and the manufacturer's protocol was followed. For western blot, protein concentration was measured by a Pierce™ BCA Protein assay kit (ThermoScientific) and 20 μg was loaded into each well of 4-20% Mini-PROTEAN TGX Precast Protein gels (Bio-Rad). After transferring the gel onto a PVDF membrane, detection of CILP was conducted by incubating the membrane with primary antibody followed by secondary antibody conjugated with HRP (Table 2). The signal was developed using the Pierce® ECL Western Blotting Substrate (ThermoScientific).

Statistical Analysis

Continuous data are presented using the mean±standard error of the mean (SEM) and comparisons between groups were performed using Student's t-test. A p-value <0.05 was considered statistically significant and data were analyzed using GraphPad Prism 6.

Results

Murine Cardiac Fibroblasts Express Ltbp2, Comp, and Cilp after Injury

Figures 1A, 1B, 1C:
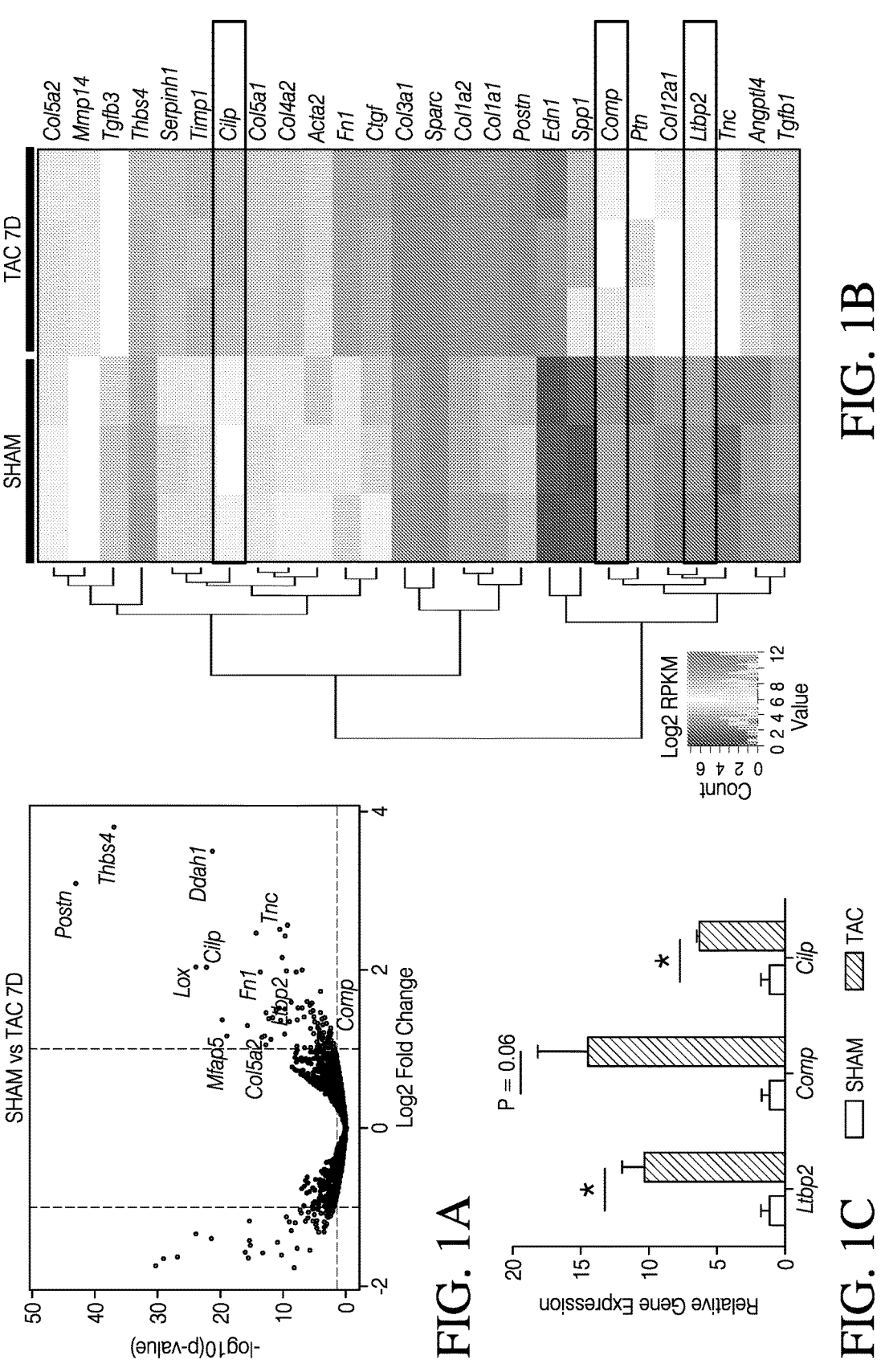
FIGS. 1A-1C. Identification of potential biomarkers for cardiac fibrosis. (1A) Volcano plot depicting highly differentially expressed genes in cardiac fibroblasts after TAC. (1B) Heatmap of pro-fibrotic genes that are upregulated in cardiac fibroblasts isolated from sham and TAC mouse hearts. Select genes (Ltbp2, Comp, and Cilp) are boxed. (1C) RT-qPCR confirmation of upregulation of Ltbp2, Comp, and Cilp in cardiac fibroblasts after 7D TAC (n=3). TAC: Transverse Aortic Constriction. P*<0.050 (t-test).

To identify secreted proteins expressed by CFbs in fibrotic hearts, we conducted RNA-sequencing on isolated CFbs from female C57BL/6J adult mice (8-12 weeks) that had undergone either sham or TAC surgery (n=3). CFbs were isolated seven days after surgery to observe gene expression changes in the early stages of fibrosis (8). After TAC, many genes were differentially expressed in CFbs (FIG. 1A, Table 3). Specifically, CFbs from mice that had undergone TAC showed higher expression of various genes associated with fibrosis (FIG. 1B). From these, we selected genes that encoded for secreted proteins and then further filtered the list to those that were novel in the context of heart failure and had previously reported roles in extracellular matrix formation/remodeling. We identified Ltbp2, Comp, and Cilp as potential candidate biomarkers. These results were further validated by RT-qPCR (FIG. 1C).

Figures 7A, 7B:
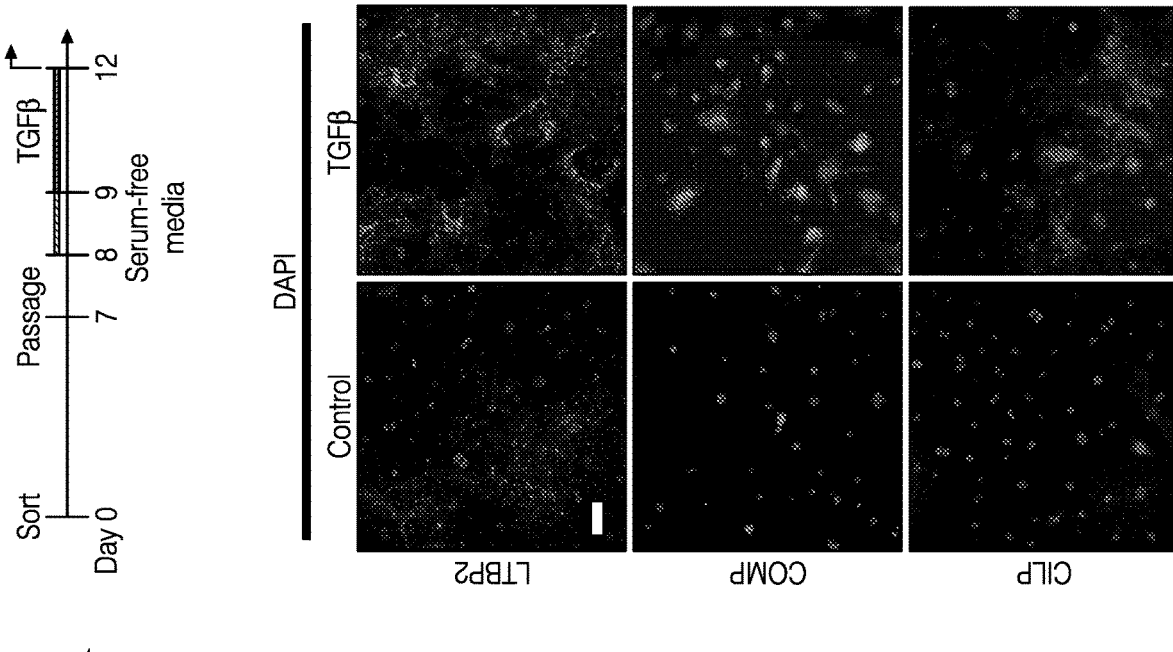
FIGS. 7A-7B. LTBP2, COMP, and CILP are upregulated in Thy1+ sorted cardiac fibroblasts after TGFβ treatment.

The TGFβ signaling pathway is a major component of injury response in cardiac fibroblasts (14). Treatment of fibroblasts in vitro with TGFβ activates and induces proliferation of cultured cells, imitating in vivo responses (15). To confirm that the TGFβ signaling pathway stimulates a robust increase in the expression of the identified genes, CFbs from uninjured C57BL/6J mice were cultured in media with or without TGFβ for 72 hours (FIG. 2A). CFbs were isolated by whole explant culture to encompass the entire CFb population in the heart, rather than a subpopulation (16). TGFβ treatment induced expression of fibroblast activation genes, such as Periostin (Postn) and α-smooth muscle actin (Acta2) (17), as well as Ltbp2, Comp, and Cilp (FIG. 2B). Furthermore, immunocytochemistry (ICC) confirmed that expression of LTBP2, COMP, and CILP were increased at the protein level in cultured CFbs after exposure to TGFβ (FIG. 2C). We observed similar patterns of staining for these proteins when CFbs were isolated by fluorescence-activated cell sorting (FIG. 7) (8). These data confirm that CFbs are a cellular source of LTBP2, COMP, and CILP under stimulatory conditions.

LTBP2, COMP, and CILP are Localized to Fibrotic Regions

Figures 3A, 3B:
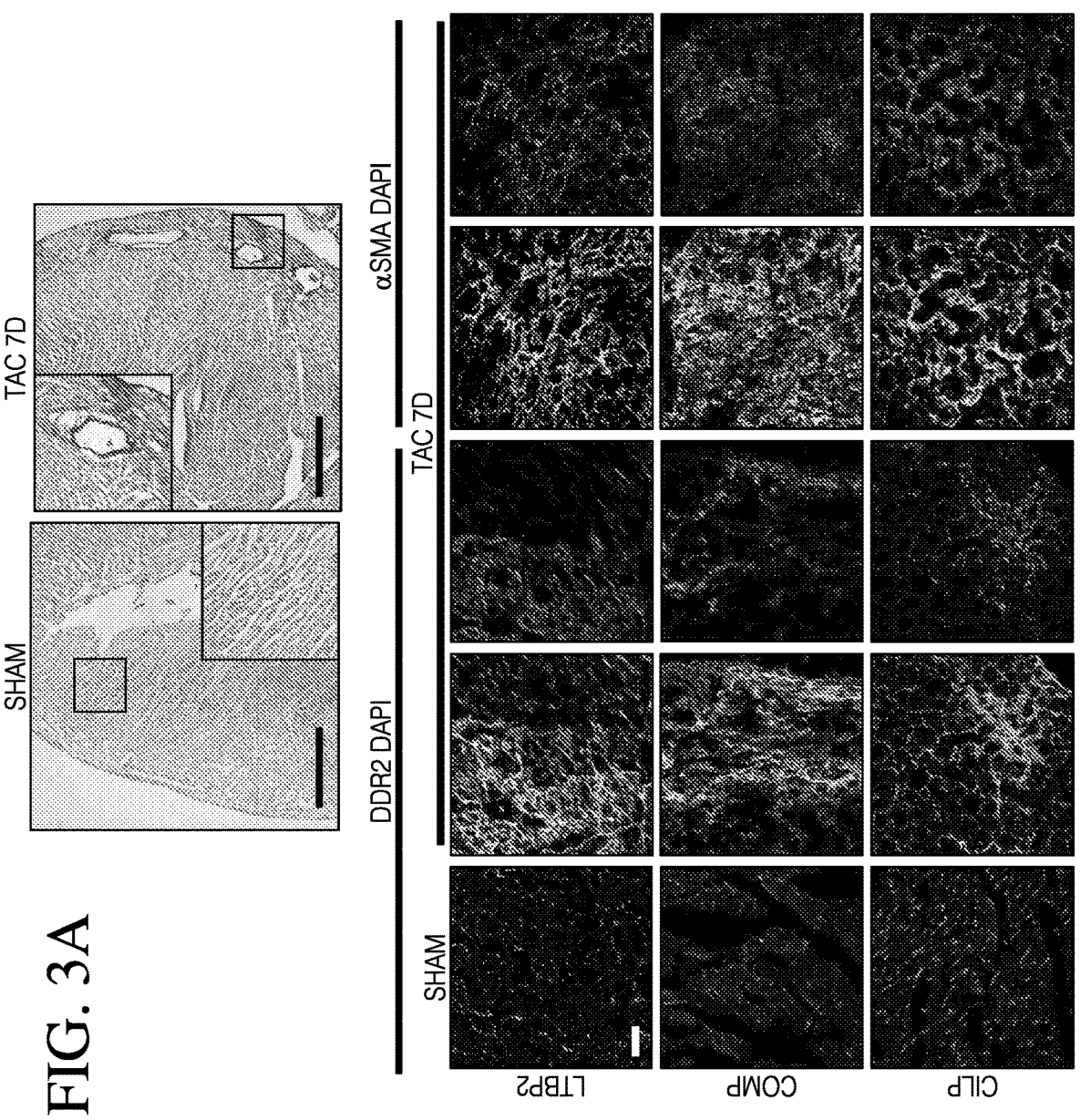
FIGS. 3A-3B. LTBP2, COMP, and CILP localize to the fibrotic myocardium. (3A) Mice that had undergone TAC surgery exhibited myocardial fibrosis as shown by Masson's trichrome staining. (3B) Immunofluorescence staining shows colocalization of LTBP2, COMP, and CILP with fibroblast marker DDR2 (left) and activated fibroblast marker αSMA (right). Red channel (LTBP2, COMP, and CILP) images are shown separately for clarity. DAPI stained for nuclei. Scale bar: 50 μm. DDR2: Discoidin Domain Receptor Tyrosine Kinase 2. αSMA: α-Smooth Muscle Actin.

Although TAC surgery induces fibrosis, it also causes other cardiac pathologies, such as hypertrophy (18). In order to confirm that the increase in LTBP2, COMP, and CILP expression after injury was specific to scar formation, we analyzed the anatomic location of LTBP2, COMP, and CILP in the hearts of mice that had undergone TAC surgery. After seven days, there was visible perivascular and interstitial fibrosis in TAC hearts, compared to sham which exhibited no fibrosis (FIG. 3A). Immunofluorescence (IF) staining showed minimal expression of the three proteins in sham hearts. In TAC hearts, LTBP2, COMP, and CILP expression appeared to colocalize with Discoidin domain-containing receptor 2 (DDR2), a marker for fibroblasts (19), and α-smooth muscle actin (αSMA) (20) within the fibrotic regions of the myocardium in TAC hearts (FIG. 3B). Areas of nonfibrotic myocardium in TAC hearts did not stain for any of the target proteins, indicating that expression of LTBP2, COMP, and CILP are expressed by activated cardiac fibroblasts and localized to regions of fibrosis.

We next sought to determine whether the expression of these biomarkers is also observed in other types of cardiac fibrosis, such as replacement fibrosis after myocardial infarction. Our findings were further confirmed in an ischemic reperfusion (IR) injury model in which the hearts exhibited discrete areas of fibrosis, although not to the severity of TAC injury. LTBP2, COMP, and CILP were found to be specifically co-localized with DDR2 and αSMA in hearts that had undergone IR (FIG. 8). Together, these data suggest that LTBP2, COMP and CILP are expressed by activated cardiac fibroblasts and are localized to regions of fibrosis.

Human Cardiac Fibroblasts have Increased LTBP2, COMP, and CILP Levels in Response to TGFβ 1 Treatment To confirm the clinical utility of our identified proteins as biomarkers for cardiac fibrosis, we sought to assess their expression levels in human ischemic myocardial tissue. RNA-sequencing data of human cardiac tissue from ischemic heart failure patients in a publicly available database (GSE46224) demonstrated that LTBP2, COMP, and CILP are upregulated in ischemic hearts (FIG. 4A) (21). We next cultured human CFbs and treated them with TGFβ 1 to stimulate their in vitro activation (FIG. 4B). TGFβ 1 treatment led to morphological changes in human CFbs and induced expression of LTBP2, COMP, and CILP, along with fibroblast activation genes (FIG. 4C). ICC staining confirmed the upregulation of LTBP2, COMP, and CILP in response to TGFβ 1 treatment, as seen in mouse CFbs (FIG. 4D). Conditioned media from cells that had undergone TGFβ 1 treatment did not show significant differences in the levels of LTBP2, an increasing trend of COMP levels, and decreased levels of CILP (FIG. 9). These results may be due to unknown mechanisms of protein secretion that affect the presence of these proteins in the context of our culture protocol. The results from the in vitro culture of human CFbs mirrored our data from mice, further supporting the potential of these proteins to be biomarkers for cardiac fibrosis.

LTBP2, COMP, and CILP are Potential Biomarkers for Cardiac Fibrosis

Figure 5B:
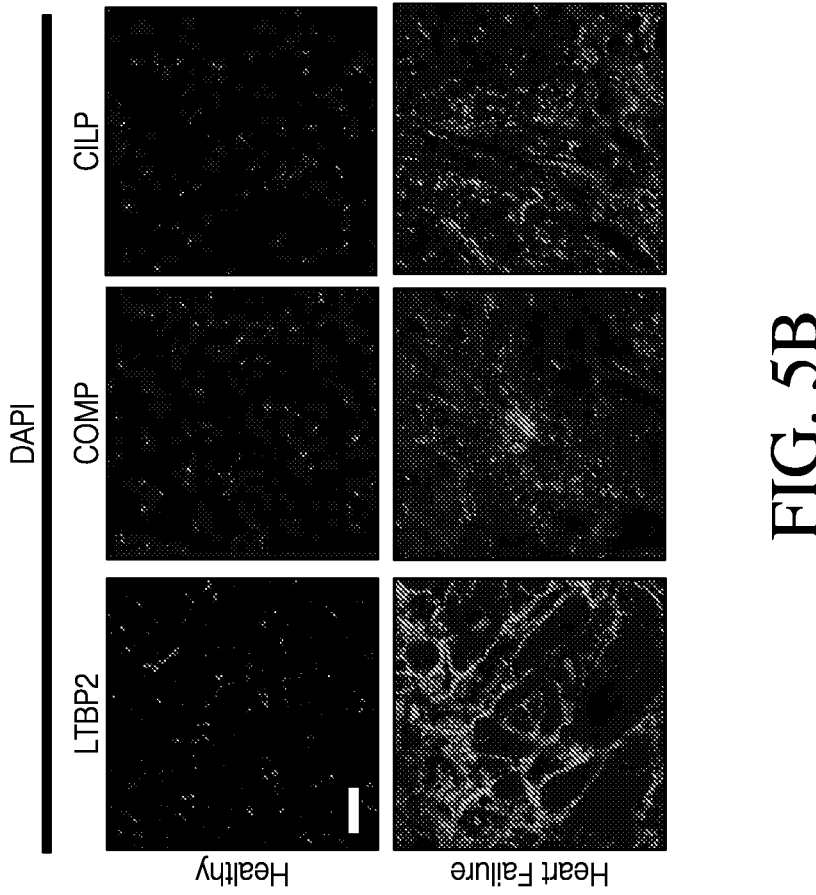
FIGS. 5A-5B. LTBP2, COMP, and CILP are upregulated in the myocardium of human heart failure patients. (5A) Masson's trichrome staining show extensive fibrosis in heart sections of heart failure patients. Insets are higher magnification images of boxed area. (5B) LTBP2, COMP, and CILP (red) expression is significantly increased in hearts undergoing heart failure. DAPI stained for nuclei. Scale bar: 50 μm.
Figure 5A:
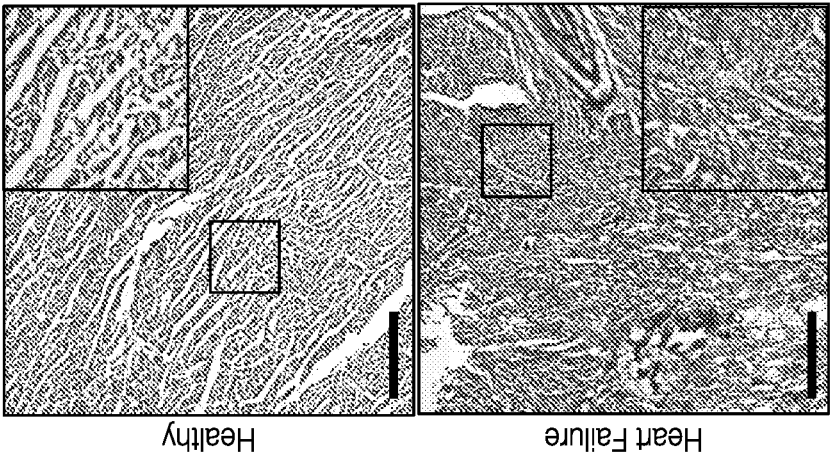

We used IF staining to observe the expression of LTBP2, COMP, and CILP within the myocardium of heart failure patients compared to healthy hearts. Myocardial tissue from heart failure patients (with a documented diagnosis of ischemic cardiomyopathy) exhibited significant amounts of fibrosis compared to healthy hearts (FIG. 5A). In healthy hearts, we observed no or minimal positive staining for the candidate markers throughout the myocardium (FIG. 5B). However, sections from diseased hearts demonstrated a significant increase in expression of all three proteins (FIG. 5B). Staining for these three proteins were localized to disarrayed regions of the myocardium, indicative of the specificity of these proteins for fibrotic areas.

Figure 6B:
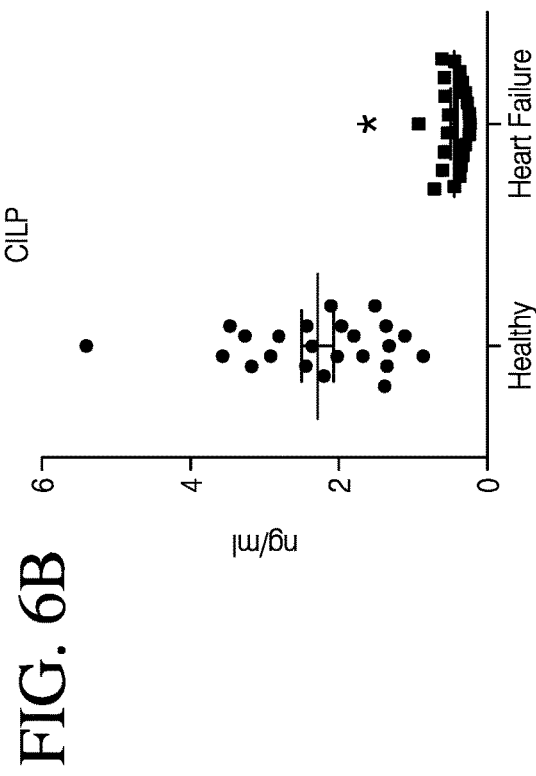
FIGS. 6A-6D. Full length CILP is downregulated in the serum of heart failure patients. (6A) ELISA demonstrates non-significant changes in levels of COMP in the serum of heart failure patients compared to healthy individuals (Healthy n=23, Heart Failure n=22). (6B) Heart failure patients had a significant decrease in circulating CILP levels (Healthy n=23, Heart Failure n=22). (6C) Representative western blotting shows decreased levels of full length CILP (~133 kDa) in heart failure patient serum. Quantified data is shown in (6D) (Healthy n=5, Heart Failure n=5). a.u.: arbitrary units. *P<0.050 (t-test).
Figure 6D:
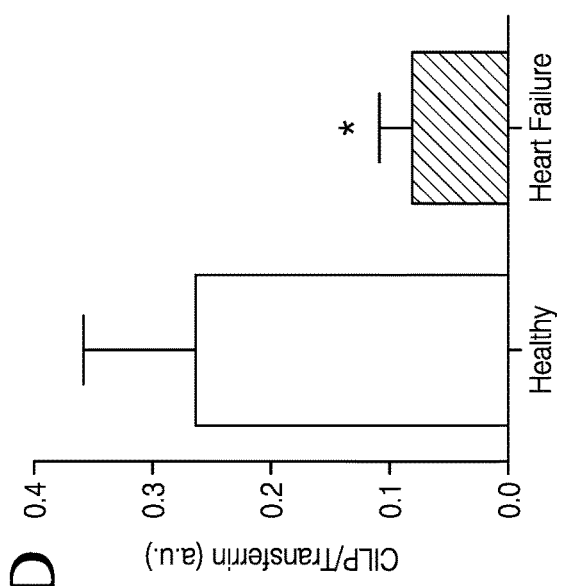
Figure 6A:
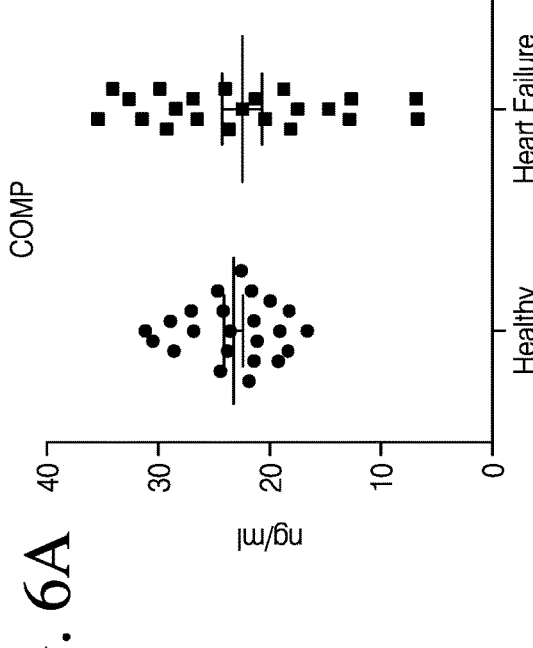
Figure 6C:
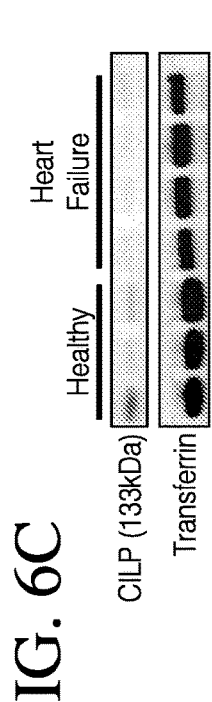

Full Length CILP is Significantly Decreased in Serum from Heart Failure Patients In addition to increased expression within the fibrotic myocardium, we sought to determine the utility of LTBP2, COMP, and CILP as novel circulating biomarkers for cardiac fibrosis. We measured the protein levels in serum from healthy volunteers and heart failure patients by ELISA (Table 4). We observed no significant differences in the circulating levels of LTBP2 (22) or COMP (FIG. 6A). However, serum from heart failure patients exhibited significantly decreased levels of CILP (FIG. 6B). Mice that had undergone TAC injury exhibited a similar trend in decreased levels of circulating CILP compared to sham mice (FIG. 10). The CILP gene encodes a precursor protein that undergoes cleavage into an N-terminal fragment of roughly 75 kDa and a C-terminal fragment of about 55 kDa (23). Both of these fragments were shown to inhibit Smad3 phosphorylation, which is normally promoted by active TGFβ signaling. While commercially available ELISA kits target the C-terminal region of CILP (hence detecting both the C-terminal and the full-length fragment), previous work discovered that CFbs secrete the N-terminal fragment as well as the full-length CILP protein (24). We specifically used an antibody that spans the cleavage site of the CILP precursor and performed western blotting to confirm levels of circulating full-length CILP. Our results showed that serum from heart failure patients had significantly decreased levels of full-length CILP in circulation (FIG. 6C-D). Together, these data suggest while activated fibroblasts in the fibrotic regions of human myocardium express high levels of CILP, the circulating level of CILP is significantly reduced when compared to healthy individuals with no evidence of cardiac fibrosis.

Discussion

With the increasing prevalence of cardiac disease worldwide, there is significant value in identifying a robust biomarker panel to non-invasively measure the presence and progression of cardiac fibrosis. We hypothesized that, as key participants of the fibrotic response, cardiac fibroblasts may be a source of novel biomarkers for myocardial fibrosis. We performed RNA-sequencing of CFbs from TAC and sham murine hearts and identified Ltbp2, Comp, and Cilp to be upregulated in hearts after pressure overload injury. The expression of these proteins by CFbs in response to injury were validated by in vitro studies in both murine and human CFbs. Additionally, we demonstrated that these proteins localize in fibrotic regions in murine hearts after pressure overload and ischemic reperfusion injury. These findings were further confirmed by high levels of these three biomarkers in the fibrotic areas of human ischemic myocardial tissue. Notably, the circulating levels of full-length CILP protein were significantly reduced in the serum of ischemic heart failure patients compared to healthy individuals, indicating its potential to be a circulating biomarker.

LTBP2 and COMP Expression is Specific to Fibrotic Regions

LTBP2 is a member of the latent TGFβ-binding protein family, which consists of key regulators of TGFβ signaling. TGFβ has diverse and pleiotropic effects on various cell types through its binding and activation of TGFβ receptors (14, 25). TGFβ is secreted from cells as a multiplex form that is covalently bound to latent TGFβ binding proteins LTBP1, LTBP3, and LTBP4. These proteins target the latent complex to specific sites for storage within the ECM where it awaits activation. Matrix sequestration of latent TGFβ may serve to regulate its immediate bioavailability while achieving critical threshold concentration at sites of intended function (9, 25). However, the functional role of LTBP2 is not well understood. Recent studies suggest that LTBP2 does not bind to latent TGFβ but may interact with other ECM proteins (9). Other studies have additionally reported on the competitive role of LTBP2 with LTBP1 for binding sites on fibrillin-1 within the ECM (26). Our data show strong support for increased expression of LTBP2 in response to injury and a strong localization of LTBP2 in activated fibroblasts within the fibrotic regions of the myocardium. Whether LTBP2 is merely a surrogate for cardiac fibrosis or is involved in its pathogenesis is not entirely known.

COMP is another ECM protein that is mainly studied in the context of tendons and cartilage (27). The main function of COMP is to directly bind with other ECM components, including collagens and TGFβ1, and to facilitate the stability of the ECM network by the formation of collagen fibrils (28). This role is crucial to maintaining homeostasis of the heart as COMP-knockout mice have been shown to develop dilated cardiomyopathy (29). However, the role of COMP in pathological remodeling is less understood. Studies have shown that COMP is upregulated in the context of idiopathic pulmonary fibrosis (30) and liver fibrosis (31), although there have been conflicting reports as to whether it can serve as an accurate circulating marker for fibrosis in patients (30,32).

Our results suggest that LTBP2 and COMP both have a strong potential for being markers for cardiac fibrosis as the expression of these proteins are specific to scar formation. However, our data does not support their use as circulating biomarkers after cardiac injury. Although these proteins are known to be secreted, it is possible that they remain within the ECM and participate in the process of fibrosis and scar formation. Further research is warranted to investigate the specific functional contributions of LTBP2 and COMP to the development of cardiac fibrosis. Due to their known roles in other organ systems, it is possible that these proteins may be markers for general fibrosis and not specific to cardiac fibrosis (33).

Decreased Levels of CILP May be Indicative of Heart Failure

The exact function of CILP within cartilage is still unknown, but it has been implicated in cartilage remodeling and maintenance of the ECM (11,34). The upregulation of CILP has been found in various disease models including osteoarthritis, idiopathic pulmonary fibrosis, and ischemic heart disease (34-37). However, the contribution of CILP to the development of cardiac fibrosis remains unknown. While most studies suggest that CFbs are the major source of CILP expression in the heart, a recent study has shown evidence of cardiomyocytes being another a major contributor (38,39). Although we did not explore the expression of CILP in cardiomyocytes, our data supports the claim that CFbs are a major cellular source of CILP. Several studies have reported that cardiac injury causes an upregulation of CILP in CFbs but the potential for CILP to be a potential biomarker for fibrosis had not been previously explored (24,39).

The CILP gene encodes for a precursor protein containing a furin cleavage site. The precursor is first synthesized and processed by furin proteases intracellularly prior to being secreted (23). The N-terminal fragment has been shown to directly interact with TGFβ, suppressing TGFβ signaling in CFbs, while the C-terminal fragment is homologous to a porcine nucleotide pyrophosphohydrolase (NTPPHase) which has been reported to have limited enzymatic activity (23,40). In contrast to the two fragments, the functional role of full-length CILP protein has not been well-studied. The full-length CILP has been shown to inhibit TGFβ signaling, similarly to the N-terminal fragment, most likely due to the common thrombospondin-1 domain which has been shown to bind to TGFβ (24). However, further studies to determine any functional differences between the N-terminal fragment and the full-length CILP are required. Our data specifically demonstrates that circulating levels of the full-length CILP are attenuated in heart failure patients but show an abundance of expression in the fibrotic myocardium. A possible mechanism for this paradox is that full-length CILP is sequestered to the ECM by its binding to TGFβ, therefore reducing circulating levels. Studies have reported that while injury induces increased expression of TGFβ in the myocardium of heart failure patients (41), circulating TGFβ is reduced (42,43). Due to the inhibitory role of full-length CILP in TGFβ signaling, it is possible that increased levels of CILP may reside in the ECM and promote a negative feedback mechanism to suppress CFb activation (24). Further studies on the dynamics of CILP turnover in the ECM are required to elucidate the significance of both circulating and interstitial CILP.

In conclusion, this Example confirms the potential for LTBP2, COMP, and CILP as novel markers of cardiac fibrosis in both mouse and human heart failure models. Most notably, we discovered a significant reduction in serum levels of full-length CILP in patients with heart failure. Biomarkers for cardiac fibrosis will serve as a noninvasive method to gain diagnostic and prognostic information regarding patients with heart failure. Our study confirms the utility of several markers of cardiac fibrosis in mouse and human subjects.

REFERENCES

1. Kong P., et al. Cell Mol Life Sci 2014; 71(4):549-74.
2. Khan R., Sheppard R. Immunology 2006; 118(1):10-24.
3. Travers J G., et al. Circ Res 2016; 118(6):1021-40.
4. Fan D., et al. Fibrogenesis & Tissue Repair 2012; 5(1):15.
5. Park S., N et al. Translational Research 2019.
6. Pitt Bertram, Zannad Faiez. Circulation: Cardiovascular Imaging 2012; 5(1):9-11.
7. Lajiness J D., Conway S J. J Cardiovasc Transl Res 2012; 5(6):739-48.
8. Ali S R., et al. Circ Res 2014; 115(7):625-35.
9. Robertson I B., et al. Matrix Biology 2015; 47:44-53.
10. Acharya C., et al. Matrix Biology 2014; 37:102-11.
11. Lorenzo P., et al. J Biol Chem 1998; 273(36):23463-8.
12. Love M I., et al. Genome Biology 2014; 15(12):550.
13. Blighe K. EnhancedVolcano: Publication-ready volcano plots with enhanced colouring and labeling. R Package Version 1.2.0 2019. Available at: github.com/kevinblighe/EnhancedVolcano.
14. Meng X-M., et al. Nat Rev Nephrol 2016; 12(6):325-38.
15. Clark R A., et al. J Cell Physiol 1997; 170(1):69-80.
16. Lynch M D., Watt F M. J Clin Invest 2018; 128(1):26-35.
17. Snider Paige, et al. Circulation Research 2009; 105(10):934-47.
18. Patten Richard D., Hall-Porter Monica R. Circulation: Heart Failure 2009; 2(2):138-44.
19. Goldsmith E C., et al. Dev Dyn 2004; 230(4):787-94.
20. Leslie K O., et al. Am J Pathol 1991; 139(1):207-16.
21. Yang K-C., et al. Circulation 2014; 129(9):1009-21.
22. Park S., et al. Circulation 2018; 138:1224-1235.
23. Lorenzo P., et al. J Biol Chem 1998; 273(36):23469-75.
24. Shindo K., et al. International Journal of Gerontology 2017; 11(2):67-74.
25. Dobaczewski M., et al. J Mol Cell Cardiol 2011; 51(4):600-6.
26. Hirani R., et al. Matrix Biol 2007; 26(4):213-23.
27. Hedbom E., et al. J Biol Chem 1992; 267(9):6132-6.
28. Rosenberg K., et al. J Biol Chem 1998; 273(32):20397-403.
29. Huang Y., et al. Basic Res Cardiol 2013; 108(5):374.
30. Vuga L J., et al. PLoS ONE 2013; 8(12):e83120.
31. Magdaleno F., et al. J Hepatol 2016; 65(5):963-71.
32. Hesselstrand R., et al. Rheumatology (Oxford) 2012; 51(5):915-20.
33. Zachou K., et al. Eur J Intern Med 2017; 38:83-8.
34. Bernardo B C., et al. J Biol Chem 2011; 286(43):37758-67.
35. Luzina I G., et al. Cell Immunol 2018; 325:1-13.
36. Sanders Y Y., et al. Am J Respir Crit Care Med 2012; 186(6):525-35.
37. Barallobre-Barreiro, J. et al. Circulation 2012; 125(6):789-802.
38. Zhang C-L., et al. Journal of Molecular and Cellular Cardiology 2018; 116:135-44.
39. Nieuwenhoven F A van., et al. Scientific Reports 2017; 7(1):16042.
40. Seki S., et al. Nature Genetics 2005; 37(6):607-12.
41. Edgley A J., et al. Cardiovascular Therapeutics 2012; 30(1):e30-40.
42. Aukrust P., et al. The American Journal of Cardiology 1999; 83(3):376-82.

43. Kapur Navin K. Circulation: Heart Failure 2011; 4(1): 5-7.

Example 2: Additional Methods and Tables

This Example describes further details of the methods employed in Example 1. In addition, Tables referenced in Example 1 can be found below.

RNA-Sequencing and Analysis

To identify potential candidates for secreted biomarkers of cardiac fibrosis, we first identified genes that were differentially expressed in cardiac fibroblasts after transverse aortic constriction compared to sham operation (GSE51620) ($p<0.05$). We selected for genes that exhibited a minimum fold-change increase of 4 to select for significantly upregulated genes in TAC. We then identified genes that were associated with fibrosis through the literature and screening for genes associated with the following Gene Ontology classes: GO:0062023 (collagen-containing extracellular matrix), GO:0001666 (response to hypoxia), GO:0001968 (fibronectin binding), GO:0030199 (collagen fibril organization), GO:0005201 (extracellular matrix structural constituent) and/or GO:0005615 (extracellular space). From this list, we further selected for genes that encoded for at least one protein product that was reportedly secreted. This was identified using online resources such as Uniprot, the Human Protein Atlas, and previously published literature. This process allowed for the selection of only secreted proteins that may mark the presence of cardiac fibrosis.

Validation of secreted proteins that were identified by our RNA sequencing was conducted using a different cardiac injury, treatment with isoproterenol (ISO). C57BL/6J mice were implanted with ALZET osmotic pumps in the abdominal cavity while under anesthesia with isoflurane. The pumps were filled with saline or ISO (Sigma) at a concentration to treat the mice at a rate of 30 mg/kg body weight/day for a treatment period of 21 days. Mouse serum was collected at the end of the treatment period and prepared for analysis as described in the section titled "Serum Preparation". Western blot and ELISA were used to screen through potential secreted proteins. Proteins that demonstrated a notable difference between saline- and ISO-treated samples were further selected for experiments.

Transverse Aortic Constriction Surgery, Ischemic-Reperfusion Surgery, and Aftercare Adult C57BL/6J mice were anesthetized by intraperitoneal injection of ketamine/xylazine (100 mg/10 mg/kg). Endotracheal intubation was performed using a blunt 20-gauge needle connected to a volume-cycled rodent ventilator (SAR-830/P; CWE, Inc.) with a tidal volume of 0.2 ml and a respiratory rate of 120/min. For transverse aortic constriction surgery, the chest was opened to expose the transverse aorta, located through the second intercostal space. Aortic constriction was performed by tying a 7-0 nylon suture ligature against a 27-gauge blunt needle and then removing the needle to yield a constriction of roughly 0.4 mm in diameter. For ischemic-reperfusion surgery, left thoracotomy between ribs four and five was performed. The pericardium was opened, and a suture was placed around the left anterior descending coronary artery 1-2 mm from the tip of the left atrium. The suture was tightened to occlude blood flow for 45 minutes and subsequently removed. Mice that underwent sham operations underwent the same procedure, excluding the constriction/occlusion. After the operation, the chest was closed in layers using 5-0 Vicryl sutures and the mice remained on the ventilators until sufficient spontaneous breathing was resumed, at which point the endotracheal tube was removed. The entire surgical procedure was performed under aseptic conditions. Buprenorphine (0.1 mg/kg) was administrated by subcutaneous injection immediately prior to surgery, followed by every 12 hours for 48 hours, and carprofen (5 mg/Kg) was administrated post operation every 24 hours for 48 hours. Mice were additionally treated post-operatively with Sulfamethoxazole and Trimethoprim oral suspension (Aurbindo). Operators blinded to the experimental designs performed all animal surgeries and in vivo analyses.

Mouse Heart Explant Fibroblast Culture

Adult C57BL/6J mice were sacrificed by isoflurane followed by cervical dislocation. Hearts were dissected from the mice and cannulated with a blunt syringe. The hearts were perfused with 20-30 ml PBS, subsequently chopped into small pieces and incubated in 7-10 ml enzyme at 37° C. on a rotator for an hour with periodic pipetting to digest larger pieces. The enzyme mix consisted of TH and TM liberases (Roche), Dnase (Invitrogen), and Poloxamer. The cells were then passed through a 70 μm filter, centrifuged, and the pellet was resuspended in DMEM containing 20% FBS, 1% Penicillin Streptomycin, and 0.1% Ciprofloxacin. The cells from one heart were plated in a single well of a 6-well plate that had been coated with 0.1% gelatin.

Immunocytochemical/Immunofluorescence Staining Detailed Protocol

For immunocytochemical staining, the fixed cells were blocked with blocking buffer (10% NGS, PBS-0.1% Tween 20™; polysorbate) for 1 hour at room temperature and then incubated in diluted primary antibodies (Table 2) overnight at 4° C. The slides were then washed 3 times with PBS-0.1% Tween™ and then incubated in diluted secondary antibodies (Table 2) for an hour at room temperature. After another round of washing with PBS-0.1% Tween 20™, the coverslips were mounted using mounting medium containing 4',6-Diamidino-2-phenylindole dihydrochloride (DAPI) (Vector Laboratories). For immunofluorescence staining, slides were incubated at room temperature for 10 minutes prior to 3 washes with PBS. The sections were treated with 0.25% Triton™ X-100 t-Octylphenoxypolyethoxyethanol in PBS to permeabilize for 10 minutes. The subsequent blocking and staining protocol mirrored immunocytochemical staining as described. Imaging was done on either a Zeiss confocal microscope (LSM880) or a Leica fluorescent microscope (LEICACTR6500). Image processing and analysis was done through either ZEN 2 (blue edition) or LAS AF Lite.

RT-qPCR Conditions

The PCR conditions for RT-qPCR had the following steps: (1) Initial denaturation—95° C. —2 minutes and 10 seconds; (2) Denaturation—95° C. —15 seconds; (3) Annealing—60° C. —30 seconds; (4) Extension—72° C. —30 seconds; (5) Repeat steps 2-4 for a total of 39 cycles; (6) Final extension—72° C. —10 minutes. The mean cycle threshold (Ct) values were taken from triplicate measurements to determine relative gene expression, as normalized to Gapdh/GAPDH expression.

Conditioned Media Preparation

Cells were cultured in 6-well plates and culture media was collected every day during the treatment period for a total of three times. The collected media was centrifuged for 10,000 rpm for 10 minutes at 4° C. and the supernatant was transferred to a separate tube to remove any cellular contamination. The media was stored at −80° C. until ready for analysis. For ELISA, the media from each day was pooled into a single sample per well. The media was concentrated by Amicon® Ultra Centrifugal Filters and the final concentrated volume was noted for total concentration calculations after ELISA.

Serum Preparation

Healthy human samples were purchased from Equitech Enterprises. Blood samples from heart failure patients were collected with informed consent (Table 4). Serum was isolated using Ficoll and stored at −80° C. until enough samples were collected for experiments. For western blots, albumin was removed from the samples with the Albu-Sorb™ Albumin Depletion Kit (Biotech Support Group).

TABLE 3

| Significantly up-regulated genes in mouse CFbs in TAC (Fold change > 4, p-value < 0.05) | | |
|---|---|---|
| Gene | FC | p-value |
| Ltbp2 | 9.866 | 2.432E−05 |
| Runx1 | 4.990 | 1.298E−04 |
| clip | 5.149 | 1.891E−04 |
| 1110006O17Rik | 5.530 | 2.261E−04 |
| Cx3cl1 | 6.097 | 3.026E−04 |

TABLE 1

| RT-qPCR Primers | | |
|---|---|---|
| Target Gene | Forward Primer (5'-3') | Reverse Primer (5'-3') |
| Gapdh (Mouse and Human) | TTGTCTCCTGCGACTTCAAC (SEQ ID NO: 2) | GTCATACCAGGAAATGAGCTTG (SEQ ID NO: 3) |
| Ltbp2 (Mouse) | AACAGCACCAACCACTGTATC (SEQ ID NO: 4) | CCTGGCATTCTGAGGGTCAAA (SEQ ID NO: 5) |
| Comp (Mouse) | ACTGCCTGCGTTCTAGTGC (SEQ ID NO: 6) | CGCCGCATTAGTCTCCTGAA (SEQ ID NO: 7) |
| Cilp (Mouse) | ATGGCAGCAATCAAGACTTGG (SEQ ID NO: 8) | AGGCTGGACTCTTCTCACTGA (SEQ ID NO: 9) |
| Acta2 (Mouse) | TGACGCTGAAGTATCCGATAGA (SEQ ID NO: 10) | CGAAGCTCGTTATAGAAAGAGTGG (SEQ ID NO: 11) |
| Ctgf (Mouse) | GACCCAACTATGATGCGAGCC (SEQ ID NO: 12) | CCCATCCCACAGGTCTTAGAA (SEQ ID NO: 13) |
| Postn (Mouse) | GACTGCTTCAGGGAGACACA (SEQ ID NO: 14) | TGATCGTCTTCTAGGCCCTT (SEQ ID NO: 15) |
| POSTN (Human) | TAGCCCAATTAGGCTTGGCATCC (SEQ ID NO: 16) | TAAGAAGGCGTTGGTCCATGCT (SEQ ID NO: 17) |
| LTBP2 (Human) | AGCACCAACCACTGTATCAAAC (SEQ ID NO: 18) | CTCATCGGGAATGACCTCCTC (SEQ ID NO: 19) |
| COMP (Human) | CAGGGAGATCACGTTCCTGA (SEQ ID NO: 20) | GGCCGGTGCGTACTGAC (SEQ ID NO: 21) |
| CILP (Human) | GCAAAAGCATCCTGAAGATCAC (SEQ ID NO: 22) | GGAGTCTCTGCCCTCACAAAC (SEQ ID NO: 23) |

45

TABLE 2

| Primary and secondary antibodies | | | |
|---|---|---|---|
| Target Protein | Technique | Catalog no. | Dilution |
| LTBP2 (Mouse/Human) | ICC | From Dr. Marko Hyytiainen (University of Helsinki, Finland) | 1:200 |
| COMP (Mouse) | ICC | Santa Cruz sc-25163 | 1:50 |
| CILP (Mouse) | ICC | Biomatik CAU24345 | 1:50 |
| DDR2 (Mouse) | IF | R&D Systems MAB25381 | 1:100 |
| aSMA (Mouse) | IF | Sigma-Aldrich A2547 | 1:100 |
| COMP (Human) | ICC | Abeam ab74524 | 1:100 |
| CILP (Human) | ICC/Western | Biomatik CAU24346 | 1:50/1:1000 |
| Secondary Target | Fluorophore | Catalog no. | Dilution |
| Anti-Rabbit IgG | Alexa Fluor ™ 488 | Invitrogen A11034 | 1:200 |
| Anti-Rabbit IgG | Alexa Fluor ™ 594 | Invitrogen A11037 | 1:200 |
| Anti-Mouse IgG | Alexa Fluor ™ 488 | Invitrogen A11029 | 1:200 |
| Anti-Rabbit IgG | HRP | Invitrogen 31460 | 1:5000 |

TABLE 3-continued

| Significantly up-regulated genes in mouse CFbs in TAC (Fold change > 4, p-value < 0.05) | | |
| --- | --- | --- |
| Gene | FC | p-value |
| Kif26b | 14.386 | 3.688E−04 |
| Casc5 | 10.002 | 4.061E−04 |
| Ass1 | 4.474 | 4.249E−04 |
| Frem1 | 21.151 | 4.304E−04 |
| Palld | 5.074 | 4.792E−04 |
| Pole | 5.574 | 5.022E−04 |
| Ncaph | 4.194 | 5.375E−04 |
| Gtse1 | 9.913 | 5.594E−04 |
| Clec11a | 4.100 | 5.617E−04 |
| EG432466 | 5.367 | 5.760E−04 |
| A930038C07Rik | 4.840 | 5.876E−04 |
| Mki67 | 8.226 | 5.932E−04 |
| Ccdc99 | 8.726 | 5.999E−04 |
| Erg | 8.030 | 6.239E−04 |
| Meox1 | 4.588 | 1.200E−03 |
| Fn1 | 5.676 | 1.343E−03 |
| Mdk | 4.842 | 1.379E−03 |
| Cenpe | 10.971 | 1.447E−03 |
| Lox | 5.109 | 1.576E−03 |
| Arhgap11a | 6.946 | 5.350E−03 |
| Cthrc1 | 28.773 | 5.914E−03 |
| Synpo | 5.143 | 5.944E−03 |
| Npl | 8.374 | 6.748E−03 |
| Col12a1 | 7.391 | 6.839E−03 |
| Col8a2 | 11.705 | 6.854E−03 |
| Dnajc15 | 5.776 | 6.930E−03 |
| Col11a1 | 45.058 | 6.980E−03 |
| Dclk3 | 5.165 | 7.230E−03 |
| Clca1 | 4.590 | 7.804E−03 |
| Adam12 | 4.649 | 7.959E−03 |
| Top2a | 6.817 | 8.380E−03 |
| Bub1 | 9.958 | 8.398E−03 |
| Cst6 | 4.562 | 8.483E−03 |
| 1500015010Rik | 7.017 | 8.553E−03 |
| Siglec1 | 8.049 | 9.065E−03 |
| Fhl2 | 4.151 | 9.132E−03 |
| 2310033K02Rik | 4.108 | 9.422E−03 |
| Pik3ap1 | 7.383 | 9.442E−03 |
| Pik3r5 | 4.736 | 9.548E−03 |
| Spink2 | 7.795 | 9.730E−03 |
| LOC100043741 | 4.470 | 1.010E−02 |
| Stoml1 | 4.101 | 1.051E−02 |
| 2810433D01Rik | 5.737 | 1.150E−02 |
| D0H4S114 | 4.442 | 1.186E−02 |
| Cenpa | 4.174 | 1.210E−02 |
| Postn | 9.933 | 1.303E−02 |
| EG620473 | 4.520 | 1.309E−02 |
| Ckap2 | 5.395 | 1.313E−02 |
| Tnc | 15.646 | 1.334E−02 |
| Hcls1 | 6.586 | 1.379E−02 |
| Pbk | 5.895 | 1.396E−02 |
| Ccl6 | 9.021 | 1.416E−02 |
| Hmmr | 9.735 | 1.420E−02 |
| Cmya3 | 5.253 | 1.474E−02 |
| Anln | 7.915 | 2.471E−02 |
| Prc1 | 5.860 | 2.482E−02 |
| Ccdc40 | 5.628 | 2.545E−02 |
| LOC621880 | 4.778 | 2.584E−02 |
| Gp49a | 4.767 | 2.597E−02 |
| 5330437I02Rik | 4.756 | 2.618E−02 |
| Kif23 | 6.567 | 2.632E−02 |
| H19 | 17.780 | 2.634E−02 |
| Nrg1 | 12.142 | 2.658E−02 |
| Tmeff1 | 6.108 | 2.783E−02 |
| LOC619973 | 4.331 | 2.801E−02 |
| 3000004C01Rik | 11.536 | 2.809E−02 |
| Cdt1 | 4.570 | 2.922E−02 |
| BC038925 | 5.308 | 2.973E−02 |
| Kif2c | 23.975 | 3.006E−02 |
| LOC100040305 | 6.952 | 3.012E−02 |
| Comtd1 | 6.332 | 3.016E−02 |
| Acan | 7.390 | 3.068E−02 |
| LOCI00043431 | 13.185 | 3.081E−02 |
| Fgfrl1 | 5.192 | 3.090E−02 |
| Kcnj15 | 4.101 | 3.231E−02 |

TABLE 3-continued

| Significantly up-regulated genes in mouse CFbs in TAC (Fold change > 4, p-value < 0.05) | | |
| --- | --- | --- |
| Gene | FC | p-value |
| Ankrd41 | 5.459 | 3.309E−02 |
| Fbxo40 | 5.599 | 3.323E−02 |
| Tpx2 | 5.887 | 3.340E−02 |
| Tm7sf2 | 4.041 | 3.436E−02 |
| Il3ra | 5.406 | 3.461E−02 |
| Pbp2 | 10.606 | 3.519E−02 |
| EG624855 | 5.004 | 3.586E−02 |
| 9930013L23Rik | 26.326 | 1.626E−03 |
| Nek2 | 6.204 | 1.878E−03 |
| Aspm | 5.494 | 1.910E−03 |
| C1qtnf6 | 4.071 | 1.914E−03 |
| LOC668063 | 13.173 | 1.944E−03 |
| Fut4 | 8.096 | 2.028E−03 |
| Cenpf | 5.151 | 2.148E−03 |
| 4930547N16Rik | 9.489 | 2.180E−03 |
| Mybl2 | 5.978 | 2.213E−03 |
| Wisp2 | 4.899 | 2.692E−03 |
| Wisp1 | 11.264 | 2.699E−03 |
| Accn2 | 5.408 | 2.815E−03 |
| Tnfrsf10b | 4.671 | 2.839E−03 |
| 5830483C08Rik | 4.309 | 3.180E−03 |
| Gpr176 | 9.108 | 3.314E−03 |
| Tlr13 | 8.906 | 4.260E−03 |
| Gmpr | 10.113 | 4.342E−03 |
| Sgol2 | 4.654 | 4.357E−03 |
| Neil3 | 9.379 | 4.391E−03 |
| LOC100043901 | 4.927 | 4.405E−03 |
| Kif15 | 14.284 | 4.641E−03 |
| EG622657 | 5.319 | 4.725E−03 |
| D530008I22 | 4.767 | 4.883E−03 |
| Thbs4 | 35.578 | 5.158E−03 |
| Fbn2 | 4.778 | 5.238E−03 |
| Ttk | 16.145 | 1.506E−02 |
| 3830403N18Rik | 6.792 | 1.517E−02 |
| Lhfpl1 | 10.304 | 1.538E−02 |
| Matn3 | 14.104 | 1.557E−02 |
| Gdf6 | 4.978 | 1.576E−02 |
| 1600015H20Rik | 4.691 | 1.581E−02 |
| Tlr5 | 6.436 | 1.594E−02 |
| Fmod | 4.628 | 1.613E−02 |
| Crlf1 | 12.408 | 1.623E−02 |
| Psrd | 6.821 | 1.624E−02 |
| Comp | 4.697 | 1.680E−02 |
| Soat2 | 8.366 | 1.695E−02 |
| 6330512M04Rik | 10.837 | 1.699E−02 |
| 1500005K14Rik | 6.481 | 1.714E−02 |
| Camk2n2 | 4.614 | 1.743E−02 |
| Zdhhc12 | 4.614 | 1.743E−02 |
| Gm22 | 4.101 | 1.794E−02 |
| Ckap2I | 22.239 | 1.796E−02 |
| 4921517D22Rik | 6.339 | 1.864E−02 |
| Ddah1 | 33.473 | 1.917E−02 |
| LOC100043526 | 8.292 | 1.934E−02 |
| Nanp | 6.634 | 1.942E−02 |
| Ccdc122 | 7.697 | 1.946E−02 |
| Pmch | 5.984 | 1.960E−02 |
| 5730590G19Rik | 17.335 | 2.084E−02 |
| Gm444 | 4.428 | 2.102E−02 |
| Iqgap3 | 4.773 | 2.144E−02 |
| LOC667005 | 6.256 | 2.193E−02 |
| Scube2 | 26.108 | 2.221 E−02 |
| Raegap1 | 4.186 | 2.236E−02 |
| Bub1b | 8.066 | 2.268E−02 |
| Depdc1a | 6.871 | 2.289E−02 |
| Ccl5 | 5.734 | 2.411 E−02 |
| LOC665939 | 5.978 | 2.435E−02 |
| Ngef | 4.325 | 2.445E−02 |
| Cep55 | 5.174 | 3.597E−02 |
| Edn1 | 6.339 | 3.602E−02 |
| D230039L06Rik | 12.520 | 3.613E−02 |
| Diap3 | 4.384 | 3.695E−02 |
| Ccna2 | 4.552 | 3.780E−02 |
| Trim29 | 4.913 | 3.819E−02 |
| Cx3cr1 | 4.900 | 3.846E−02 |
| Nxt1 | 5.255 | 3.904E−02 |

TABLE 3-continued

Significantly up-regulated genes in mouse CFbs in TAC
(Fold change > 4, p-value < 0.05)

| Gene | FC | p-value |
|---|---|---|
| Ptn | 10.726 | 3.909E–02 |
| Zfp185 | 6.172 | 4.021E–02 |
| Cit | 6.924 | 4.073E–02 |
| LOC100038957 | 5.608 | 4.199E–02 |
| EG432951 | 6.210 | 4.254E–02 |
| Pdgfc | 5.766 | 4.327E–02 |
| EG218444 | 4.344 | 4.335E–02 |
| Sfrp2 | 4.335 | 4.455E–02 |
| Ccnb2 | 5.077 | 4.539E–02 |
| Kif4 | 13.148 | 4.542E–02 |
| 5033413D22Rik | 5.739 | 4.612E–02 |
| Lilrb4 | 4.658 | 4.663E–02 |
| Gpr65 | 6.596 | 4.675E–02 |
| Tmem132e | 6.594 | 4.675E–02 |
| Padi4 | 4.066 | 4.686E–02 |
| Bcas1 | 6.097 | 4.725E–02 |
| Cdca7 | 4.606 | 4.758E–02 |
| EspH | 4.174 | 4.914E–02 |
| Ect2 | 20.594 | 4.918E–02 |

TABLE 4

Characteristics of human samples

| | Healthy Individuals (n = 23) | HF Patients (n = 22)* |
|---|---|---|
| Age (years) | 50 ± 10 | ≤40: 5%<br>41-50: 18%<br>51-60: 27%<br>61-70: 36%<br>≥71: 14% |
| Gender | M: 50%<br>F: 50% | M: 64%<br>F: 36% |
| Etiology | N/A | 59% Ischemic<br>41% Non-iCMY |
| EF (%) | ≥55 | 15: 9%<br>20: 23%<br>25: 27%<br>30: 27%<br>35: 14% |
| Median BNP (pg/ml)<br>Mean [IQR] | N/A | 696 [507-850] |

TABLE 4-continued

Characteristics of human samples

| | | |
|---|---|---|
| DM | 0% | Y: 37%<br>N: 63% |
| h/o HTN | 0% | Y: 45%<br>N: 50% |
| Medications | N/A | D: 73%<br>BB: 100%<br>Ent: 41%<br>ACE–1: 32%<br>ARB: 18%<br>AA: 36% |

| | Healthy Individuals (n = 23) | HF Patients (n = 22)* |
|---|---|---|
| Age (years) | 50 ± 10 | 59 ± 10 |
| Gender | 50% M<br>50% F | 64% M<br>36% F |
| Etiology | N/A | 59% Ischemic<br>41% Non-iCMY |
| EF (%) | ≥55 | 26 ± 6 |
| Median BNP (pg/ml) | N/A | 696 ± 369 |
| DM | 0% | Y: 37%<br>N: 63% |
| h/o HTN | 0% | Y: 45%<br>N: 50% |
| Medications | N/A | D: 73%<br>BB: 100%<br>Ent: 41%<br>ACE-I: 32%<br>ARB: 18%<br>AA: 36% |

*Abbreviations: Non-iCMY: Non-ischemic cardiomyopathy; D: Diuretics; BB: Beta blockers; Ent: Entresto; ACE–I: Ace-inhibitors; ARB: Angiotensin receptor blockers; AA: Aldosterone antagonists Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating cardiac fibrosis, progression of cardiac fibrosis, or heart failure in a subject, the method comprising:

(a) contacting a serum sample obtained from the subject with an antibody that binds a region of cartilage intermediate layer protein 1 (CILP) that spans the cleavage site of a CILP precursor;

(b) measuring a decrease in the amount of CILP in the serum sample relative to a reference sample; and (c) treating the subject for cardiac fibrosis, progression of cardiac fibrosis, or heart failure when the amount of CILP in the serum sample is decreased relative to a reference sample.

2. The method of claim 1, wherein the treatment comprises administering to the subject one or more of: angiotensin (AT)-converting enzymes, ATI receptor antagonists, β-blockers, Sacubitril/Valsartan, Aldosterone antagonists, statins, or diuretics.

3. The method of claim 1, wherein the reference sample is from a normal, healthy control subject.

4. The method of claim 1, wherein the reference sample is a previously obtained sample from the subject.

5. The method of claim 1, wherein the antibody binds to full-length CILP.

6. The method of claim 1, further comprising measuring up to 10 additional biomarkers.

7. The method of claim 6, wherein the additional biomarkers comprise biomarkers selected from B-type natriuretic peptide (BNP); or its stable precursor NT-proBNP, Galectin-3 (Gal-3), suppression of tumorigenicity 2 (ST2), latent transforming growth factor beta (LTBP2), and cartilage oligomeric matrix protein (COMP).

8. The method of claim 1, wherein the cardiac fibrosis is associated with one or more of: ischemia, congenital defect, familial fibrosis, infiltrative fibrosis, idiopathic fibrosis, amyloidosis, hemosiderosis, and valvular disease.

* * * * *

SEQUENCE LISTING

```
<160> NUMBER OF SEQ ID NOS: 23

<210> SEQ ID NO 1
<211> LENGTH: 1184
<212> TYPE: PRT
<213> ORGANISM: Homo sapiens

<400> SEQUENCE: 1

Met Val Gly Thr Lys Ala Trp Val Phe Ser Phe Leu Val Leu Glu Val
1               5                   10                  15

Thr Ser Val Leu Gly Arg Gln Thr Met Leu Thr Gln Ser Val Arg Arg
            20                  25                  30

Val Gln Pro Gly Lys Lys Asn Pro Ser Ile Phe Ala Lys Pro Ala Asp
        35                  40                  45

Thr Leu Glu Ser Pro Gly Glu Trp Thr Thr Trp Phe Asn Ile Asp Tyr
    50                  55                  60

Pro Gly Gly Lys Gly Asp Tyr Glu Arg Leu Asp Ala Ile Arg Phe Tyr
```

```
65                  70                  75                  80

Tyr Gly Asp Arg Val Cys Ala Arg Pro Leu Arg Leu Glu Ala Arg Thr
                85                  90                  95

Thr Asp Trp Thr Pro Ala Gly Ser Thr Gly Gln Val Val His Gly Ser
            100                 105                 110

Pro Arg Glu Gly Phe Trp Cys Leu Asn Arg Glu Gln Arg Pro Gly Gln
        115                 120                 125

Asn Cys Ser Asn Tyr Thr Val Arg Phe Leu Cys Pro Pro Gly Ser Leu
    130                 135                 140

Arg Arg Asp Thr Glu Arg Ile Trp Ser Pro Trp Ser Pro Trp Ser Lys
145                 150                 155                 160

Cys Ser Ala Ala Cys Gly Gln Thr Gly Val Gln Thr Arg Thr Arg Ile
                165                 170                 175

Cys Leu Ala Glu Met Val Ser Leu Cys Ser Glu Ala Ser Glu Glu Gly
            180                 185                 190

Gln His Cys Met Gly Gln Asp Cys Thr Ala Cys Asp Leu Thr Cys Pro
        195                 200                 205

Met Gly Gln Val Asn Ala Asp Cys Asp Ala Cys Met Cys Gln Asp Phe
    210                 215                 220

Met Leu His Gly Ala Val Ser Leu Pro Gly Gly Ala Pro Ala Ser Gly
225                 230                 235                 240

Ala Ala Ile Tyr Leu Leu Thr Lys Thr Pro Lys Leu Leu Thr Gln Thr
                245                 250                 255

Asp Ser Asp Gly Arg Phe Arg Ile Pro Gly Leu Cys Pro Asp Gly Lys
            260                 265                 270

Ser Ile Leu Lys Ile Thr Lys Val Lys Phe Ala Pro Ile Val Leu Thr
        275                 280                 285

Met Pro Lys Thr Ser Leu Lys Ala Ala Thr Ile Lys Ala Glu Phe Val
    290                 295                 300

Arg Ala Glu Thr Pro Tyr Met Val Met Asn Pro Glu Thr Lys Ala Arg
305                 310                 315                 320

Arg Ala Gly Gln Ser Val Ser Leu Cys Cys Lys Ala Thr Gly Lys Pro
                325                 330                 335

Arg Pro Asp Lys Tyr Phe Trp Tyr His Asn Asp Thr Leu Leu Asp Pro
            340                 345                 350

Ser Leu Tyr Lys His Glu Ser Lys Leu Val Leu Arg Lys Leu Gln Gln
        355                 360                 365

His Gln Ala Gly Glu Tyr Phe Cys Lys Ala Gln Ser Asp Ala Gly Ala
        370                 375                 380

Val Lys Ser Lys Val Ala Gln Leu Ile Val Ile Ala Ser Asp Glu Thr
385                 390                 395                 400

Pro Cys Asn Pro Val Pro Glu Ser Tyr Leu Ile Arg Leu Pro His Asp
                405                 410                 415

Cys Phe Gln Asn Ala Thr Asn Ser Phe Tyr Tyr Asp Val Gly Arg Cys
            420                 425                 430

Pro Val Lys Thr Cys Ala Gly Gln Gln Asp Asn Gly Ile Arg Cys Arg
        435                 440                 445

Asp Ala Val Gln Asn Cys Cys Gly Ile Ser Lys Thr Glu Glu Arg Glu
    450                 455                 460

Ile Gln Cys Ser Gly Tyr Thr Leu Pro Thr Lys Val Ala Lys Glu Cys
465                 470                 475                 480

Ser Cys Gln Arg Cys Thr Glu Thr Arg Ser Ile Val Arg Gly Arg Val
                485                 490                 495
```

```
Ser Ala Ala Asp Asn Gly Glu Pro Met Arg Phe Gly His Val Tyr Met
        500                 505             510

Gly Asn Ser Arg Val Ser Met Thr Gly Tyr Lys Gly Thr Phe Thr Leu
        515                 520             525

His Val Pro Gln Asp Thr Glu Arg Leu Val Leu Thr Phe Val Asp Arg
        530                 535             540

Leu Gln Lys Phe Val Asn Thr Thr Lys Val Leu Pro Phe Asn Lys Lys
545                 550                 555             560

Gly Ser Ala Val Phe His Glu Ile Lys Met Leu Arg Arg Lys Lys Pro
                565                 570             575

Ile Thr Leu Glu Ala Met Glu Thr Asn Ile Ile Pro Leu Gly Glu Val
        580                 585             590

Val Gly Glu Asp Pro Met Ala Glu Leu Glu Ile Pro Ser Arg Ser Phe
        595                 600             605

Tyr Arg Gln Asn Gly Glu Pro Tyr Ile Gly Lys Val Lys Ala Ser Val
        610                 615             620

Thr Phe Leu Asp Pro Arg Asn Ile Ser Thr Ala Thr Ala Ala Gln Thr
625                 630                 635             640

Asp Leu Asn Phe Ile Asn Asp Glu Gly Asp Thr Phe Pro Leu Arg Thr
                645                 650             655

Tyr Gly Met Phe Ser Val Asp Phe Arg Asp Glu Val Thr Ser Glu Pro
                660                 665             670

Leu Asn Ala Gly Lys Val Lys Val His Leu Asp Ser Thr Gln Val Lys
            675                 680             685

Met Pro Glu His Ile Ser Thr Val Lys Leu Trp Ser Leu Asn Pro Asp
        690                 695             700

Thr Gly Leu Trp Glu Glu Glu Gly Asp Phe Lys Phe Glu Asn Gln Arg
705                 710                 715             720

Arg Asn Lys Arg Glu Asp Arg Thr Phe Leu Val Gly Asn Leu Glu Ile
                725                 730             735

Arg Glu Arg Arg Leu Phe Asn Leu Asp Val Pro Glu Ser Arg Arg Cys
                740                 745             750

Phe Val Lys Val Arg Ala Tyr Arg Ser Glu Arg Phe Leu Pro Ser Glu
            755                 760             765

Gln Ile Gln Gly Val Val Ile Ser Val Ile Asn Leu Glu Pro Arg Thr
        770                 775             780

Gly Phe Leu Ser Asn Pro Arg Ala Trp Gly Arg Phe Asp Ser Val Ile
785                 790                 795             800

Thr Gly Pro Asn Gly Ala Cys Val Pro Ala Phe Cys Asp Asp Gln Ser
                805                 810             815

Pro Asp Ala Tyr Ser Ala Tyr Val Leu Ala Ser Leu Ala Gly Glu Glu
                820                 825             830

Leu Gln Ala Val Glu Ser Ser Pro Lys Phe Asn Pro Asn Ala Ile Gly
            835                 840             845

Val Pro Gln Pro Tyr Leu Asn Lys Leu Asn Tyr Arg Arg Thr Asp His
        850                 855             860

Glu Asp Pro Arg Val Lys Lys Thr Ala Phe Gln Ile Ser Met Ala Lys
865                 870                 875             880

Pro Arg Pro Asn Ser Ala Glu Glu Ser Asn Gly Pro Ile Tyr Ala Phe
                885                 890             895

Glu Asn Leu Arg Ala Cys Glu Glu Ala Pro Pro Ser Ala Ala His Phe
            900                 905             910
```

```
Arg Phe Tyr Gln Ile Glu Gly Asp Arg Tyr Asp Tyr Asn Thr Val Pro
        915                 920                 925

Phe Asn Glu Asp Asp Pro Met Ser Trp Thr Glu Asp Tyr Leu Ala Trp
    930                 935                 940

Trp Pro Lys Pro Met Glu Phe Arg Ala Cys Tyr Ile Lys Val Lys Ile
945                 950                 955                 960

Val Gly Pro Leu Glu Val Asn Val Arg Ser Arg Asn Met Gly Gly Thr
                965                 970                 975

His Arg Gln Thr Val Gly Lys Leu Tyr Gly Ile Arg Asp Val Arg Ser
            980                 985                 990

Thr Arg Asp Arg Asp Gln Pro Asn  Val Ser Ala Ala Cys  Leu Glu Phe
        995                 1000                1005

Lys Cys  Ser Gly Met Leu Tyr  Asp Gln Asp Arg Val  Asp Arg Thr
    1010                1015                1020

Leu Val  Lys Val Ile Pro Gln  Gly Ser Cys Arg  Ala Ser Val
    1025                1030                1035

Asn Pro  Met Leu His Glu Tyr  Leu Val Asn His Leu  Pro Leu Ala
    1040                1045                1050

Val Asn  Asn Asp Thr Ser Glu  Tyr Thr Met Leu Ala  Pro Leu Asp
    1055                1060                1065

Pro Leu  Gly His Asn Tyr Gly  Ile Tyr Thr Val Thr  Asp Gln Asp
    1070                1075                1080

Pro Arg  Thr Ala Lys Glu Ile  Ala Leu Gly Arg Cys  Phe Asp Gly
    1085                1090                1095

Thr Ser  Asp Gly Ser Ser Arg  Ile Met Lys Ser Asn  Val Gly Val
    1100                1105                1110

Ala Leu  Thr Phe Asn Cys Val  Glu Arg Gln Val Gly  Arg Gln Ser
    1115                1120                1125

Ala Phe  Gln Tyr Leu Gln Ser  Thr Pro Ala Gln Ser  Pro Ala Ala
    1130                1135                1140

Gly Thr  Val Gln Gly Arg Val  Pro Ser Arg Arg Gln  Gln Arg Ala
    1145                1150                1155

Ser Arg  Gly Gly Gln Arg Gln  Gly Gly Val Val Ala  Ser Leu Arg
    1160                1165                1170

Phe Pro  Arg Val Ala Gln Gln  Pro Leu Ile Asn
    1175                1180
```

```
<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttgtctcctg cgacttcaac                                                   20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gtcataccag gaaatgagct tg                                                 22
```

-continued

```
<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aacagcacca accactgtat c                                          21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cctggcattc tgagggtcaa a                                          21

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
actgcctgcg ttctagtgc                                             19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cgccgcatta gtctcctgaa                                            20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
atggcagcaa tcaagacttg g                                          21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
aggctggact cttctcactg a                                          21

<210> SEQ ID NO 10
<211> LENGTH: 22
<212> TYPE: DNA
<213> ORGANISM: Artificial Sequence
<220> FEATURE:
<223> OTHER INFORMATION: primer
```

-continued

```
<400> SEQUENCE: 10
tgacgctgaa gtatccgata ga                                             22

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cgaagctcgt tatagaaaga gtgg                                           24

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gacccaacta tgatgcgagc c                                              21

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cccatcccac aggtcttaga a                                              21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gactgcttca gggagacaca                                                20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tgatcgtctt ctaggccctt                                                20

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
tagcccaatt aggcttggca tcc                                            23

<210> SEQ ID NO 17
<211> LENGTH: 22
```

```
<212> TYPE: DNA
<213> ORGANISM: Artificial Sequence
<220> FEATURE:
<223> OTHER INFORMATION: primer

<400> SEQUENCE: 17
taagaaggcg ttggtccatg ct                                              22

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
agcaccaacc actgtatcaa ac                                              22

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
ctcatcggga atgacctcct c                                               21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cagggagatc acgttcctga                                                 20

<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
ggccggtgcg tactgac                                                    17

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gcaaaagcat cctgaagatc ac                                              22
```

-continued

```
<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ggagtctctg ccctcacaaa c                                          21
```